(12) United States Patent
Jarrahi

(10) Patent No.: US 10,863,895 B2
(45) Date of Patent: Dec. 15, 2020

(54) TERAHERTZ ENDOSCOPY THROUGH LASER-DRIVEN TERAHERTZ SOURCES AND DETECTORS

(71) Applicant: The Regents of the University of California, Oakland, CA (US)

(72) Inventor: Mona Jarrahi, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 33 days.

(21) Appl. No.: 15/577,222

(22) PCT Filed: May 27, 2016

(86) PCT No.: PCT/US2016/034704
§ 371 (c)(1),
(2) Date: Nov. 27, 2017

(87) PCT Pub. No.: WO2016/196309
PCT Pub. Date: Dec. 8, 2016

(65) Prior Publication Data
US 2019/0150719 A1    May 23, 2019

Related U.S. Application Data

(60) Provisional application No. 62/167,201, filed on May 27, 2015, provisional application No. 62/579,676, filed on Oct. 31, 2017.

(51) Int. Cl.
*A61B 1/06* (2006.01)
*G01J 3/42* (2006.01)
(Continued)

(52) U.S. Cl.
CPC .......... *A61B 1/063* (2013.01); *A61B 1/00188* (2013.01); *A61B 1/00195* (2013.01);
(Continued)

(58) Field of Classification Search
CPC ..... A61B 1/063; A61B 1/2736; A61B 1/2676; A61B 1/04; A61B 1/00195;
(Continued)

(56) References Cited

U.S. PATENT DOCUMENTS 6,529,093 B2    3/2003    Ma
7,321,275 B2    1/2008    Chou et al.
(Continued)

FOREIGN PATENT DOCUMENTS

EP    1804347 A1    7/2007
EP    2807675 A1    12/2014
(Continued)

OTHER PUBLICATIONS

Humphreys et al. ("Medical applications of terahertz imaging: a review of current technology and potential applications in biomedical engineering", Proceedings of the 26th Annual International Conference of the IEEE EMBS San Francisco, CA, USA September (Year: 2004).*
(Continued)

*Primary Examiner* — David P Porta
*Assistant Examiner* — Meenakshi S Sahu
(74) *Attorney, Agent, or Firm* — KPPB LLP

(57) ABSTRACT

Terahertz imaging systems for endoscopy are provided. Terahertz imaging systems can be utilized in scanning tissue. Terahertz imaging systems in accordance with embodiments of the invention can include terahertz sources, terahertz detectors, and/or rotating elements. The terahertz sources can generate terahertz radiation and have plasmonic contact electrodes that can be illuminated by optical pump beams. The terahertz detectors can receive terahertz field data. The terahertz source and detector can be arranged in an array. The rotating elements can be mirror mounted at a particular
(Continued)

US 10,863,895 B2

Page 2 angle on a micromotor. The terahertz source, rotating element, and terahertz detector can be arranged in an catheter.

20 Claims, 14 Drawing Sheets

(51) Int. Cl.
*H01L 31/0224* (2006.01)
*H01L 31/0304* (2006.01)
*H01L 31/08* (2006.01)
*G01N 21/3586* (2014.01)
*H01L 27/146* (2006.01)
*A61B 1/05* (2006.01)
*A61B 1/00* (2006.01)
*A61B 1/04* (2006.01)
*A61B 1/267* (2006.01)
*A61B 1/273* (2006.01)
*G01J 3/28* (2006.01)

(52) U.S. Cl.
CPC .................. *A61B 1/04* (2013.01); *A61B 1/05* (2013.01); *A61B 1/0676* (2013.01); *A61B 1/2676* (2013.01); *A61B 1/2736* (2013.01); *G01J 3/2823* (2013.01); *G01J 3/42* (2013.01); *G01N 21/3586* (2013.01); *H01L 27/14601* (2013.01); *H01L 31/0224* (2013.01); *H01L 31/03042* (2013.01); *H01L 31/08* (2013.01); *Y02E 10/544* (2013.01)

(58) Field of Classification Search
CPC ..... A61B 1/00188; A61B 1/0676; A61B 1/05; G01J 3/2823; G01J 3/42; H01L 31/08; H01L 31/03042; H01L 31/0224; H01L 27/14601; Y02E 10/544; G01N 21/3586
USPC ...................................................... 250/341.8
See application file for complete search history.

(56) References Cited

U.S. PATENT DOCUMENTS

| 7,834,722 | B2 | 11/2010 | Millet |
| 7,915,641 | B2 | 3/2011 | Otsuji et al. |
| 8,450,687 | B2 | 5/2013 | Lampin et al. |
| 8,466,528 | B2 | 6/2013 | Okamoto et al. |
| 8,514,403 | B2 | 8/2013 | Ogawa et al. |
| 8,581,784 | B2 | 11/2013 | Nagel |
| 9,804,026 | B2 | 10/2017 | Jarrahi et al. |
| 9,859,079 | B2 | 1/2018 | Jarrahi et al. |
| 2005/0236260 | A1 | 10/2005 | Pasch et al. |
| 2007/0278075 | A1 | 12/2007 | Terano et al. |
| 2008/0001691 | A1 | 1/2008 | Hong et al. |
| 2008/0277672 | A1 | 11/2008 | Hovey et al. |
| 2009/0259102 | A1 | 10/2009 | Koninckx et al. |
| 2009/0273532 | A1 | 11/2009 | Mendis et al. |
| 2010/0102256 | A1 | 4/2010 | Andrew et al. |
| 2010/0277726 | A1 | 11/2010 | Logan et al. |
| 2011/0028824 | A1* | 2/2011 | Cole .................... A61B 5/0062 600/407 |
| 2011/0080329 | A1 | 4/2011 | Nagel |
| 2011/0141468 | A1 | 6/2011 | Kukushkin et al. |
| 2011/0215246 | A1 | 9/2011 | Kajiki |
| 2012/0122259 | A1 | 5/2012 | Tung et al. |
| 2012/0205767 | A1 | 8/2012 | Bai et al. |
| 2012/0294549 | A1 | 11/2012 | Doepke |
| 2013/0161514 | A1 | 6/2013 | Kukushkin et al. |
| 2014/0103211 | A1 | 4/2014 | Darcie et al. |
| 2014/0198973 | A1 | 7/2014 | Zhang et al. |
| 2014/0346357 | A1* | 11/2014 | Jarrahi ................ H01L 31/0224 250/338.4 |
| 2016/0196943 | A1 | 7/2016 | Jarrahi et al. |
| 2018/0058931 | A1 | 3/2018 | Jarrahi et al. |

FOREIGN PATENT DOCUMENTS

| EP | 3302224 | A2 | 4/2018 |
| EP | 2807675 | B1 | 9/2018 |
| JP | 11056786 | A | 3/1999 |
| JP | 2002511960 | A | 4/2002 |
| JP | 2006216646 | A | 8/2006 |
| JP | 2008122278 | A | 5/2008 |
| JP | 2009105102 | A | 5/2009 |
| JP | 2009531841 | A | 9/2009 |
| JP | 2010510703 | A | 4/2010 |
| JP | 2015513067 | A | 4/2015 |
| JP | 2018516667 | A | 6/2018 |
| KR | 20080004467 | A | 1/2008 |
| WO | 1998046042 | A1 | 10/1998 |
| WO | 2006030608 | A1 | 3/2006 |
| WO | 2010021073 | A1 | 2/2010 |
| WO | 2010044193 | A1 | 4/2010 |
| WO | 2011028179 | A1 | 3/2011 |
| WO | 2011118398 | A1 | 9/2011 |
| WO | 2011129690 | A2 | 10/2011 |
| WO | 2016196309 | A2 | 12/2016 |
| WO | 2016196309 | A3 | 2/2017 |

OTHER PUBLICATIONS

European Examination Report Corresponding to EP Application No. 13741491.8, dated Oct. 21, 2015, 5 Pages.
Extended European Search Report for European Application No. 16804130.9, Search completed Jan. 16, 2019, dated Jan. 25, 2019, 6 Pgs.
International Preliminary Report on Patentability for International Application PCT/US2016/034704, Report issued Nov. 28, 2017, dated Dec. 7, 2017, 9 Pgs.
International Search Report and Written Opinion for International Application No. PCT/US2013/022776, Search completed May 15, 2013, dated May 16, 2013, 9 Pgs.
International Search Report and Written Opinion for International Application No. PCT/US2014/049866, Search completed Nov. 19, 2014, dated Nov. 20, 2014, 9 Pgs.
International Search Report and Written Opinion for International Application No. PCT/US2016/034704, Search completed Dec. 26, 2016, dated Dec. 26, 2016, 11 Pgs.
Supplementary European Search Report for European Application No. 13741491.8, Search completed Sep. 28, 2015, dated Oct 12, 2015, 06 Pgs.
Ajito et al., "THz Chemical Imaging for Biological Applications", IEEE Transactions on Terahertz Science and Technology, Sep. 2011, First Published: Aug. 30, 2011, vol. 1, No. 1, pp. 293-300, DOI: 10.1109/TTHZ.2011.2159562.
Arbab et al., "Terahertz spectroscopy for the assessment of burn injuries in vivo", Journal of Biomedical Optics, vol. 18, No. 7, Jul. 2013, pp. 077004-1-077004-7.
Ashworth et al., "Terahertz pulsed spectroscopy of freshly excised human breast cancer", Optics Express, 2009, vol. 17, No. 15, pp. 12444-12454, https://doi.org/10.1364/OE.17.012444.
Beck et al., "Impulsive terahertz radiation with high electric fields from an amplifier-driven large-area photoconductive antenna", Optics Express, 2010, vol. 18, No. 9, pp. 9251-9257, https://doi.org/10.1364/OE.18.009251.
Berry et al., "Generation of high power pulsed terahertz radiation using a plasmonic photoconductive emitter array with logarithmic spiral antennas", Applied Physics Letters, 2014, vol. 104, 081122, pp. 081122-1-081122-4.
Berry et al., "High Power Terahertz Generation Using 1550 nm Plasmonic Photomixers", Applied Physics Letters, vol. 105, pp. 011121-1-011121-4, 2014, Published online Jul. 2014.
Berry et al., "Plasmonics enhanced photomixing for generating quasi-continuous-wave frequency-tunable terahertz radiation", Optics Letters, 2014, vol. 39, No. 15, pp. 4522-4524, https://doi.org/10.1364/OL.39.004522.
Berry et al., "Significant performance enhancement in photoconductive terahertz optoelectronics by incorporating plasmonic contact electrodes", Nature Communication, vol. 4, Mar. 27, 2013, 10 pgs.

(56) References Cited

OTHER PUBLICATIONS

Berry et al., "Terahertz generation using plasmonic photoconductive gratings", New Journal of Physics, 2012, vol. 14, 12 pgs.
Chan et al., "Imaging with terahertz radiation", Reports on Progress in Physics, Jul. 12, 2007, vol. 70, No. 8, pp. 1325-1379.
Clothier et al., "Effects of THz Exposure on Human Primary Keratinocyte Differentiation and Viability", Journal of Biological Physics, 2003, vol. 29, pp. 179-185.
Dreyhaupt et al., "High-intensity terahertz radiation from a microstructured large-area photoconductor", Applied Physics Letters, 2005, vol. 86, No. 121114, 4 pgs. https://doi.org/10.1063/1.1891304.
Fitzgerald et al., "Catalogue of Human Tissue Optical Properties at Terahertz Frequencies", Journal of Biological Physics, 2003, vol. 29, pp. 123-128.
Fitzgerald et al., "Nondestructive analysis of tablet coating thicknesses using terahertz pulsed imaging", Journal of Pharmaceutical Sciences, Jan. 2005, First Published: Nov. 22, 2004, vol. 94, No. 1, pp. 177-183, https://doi.org/10.1002/jps.20225.
Gu et al., "Detection of Terahertz Radiation from Longitudinal Optical Phonon-Plasmon Coupling Modes in InSb Film Using an Ultrabroadband Photoconductive Antenna", Applied Physics Letters, American Institute of Physics, Sep. 18, 2000, vol. 77, No. 12, pp. 1798-1800.
Hu et al., "Imaging with terahertz waves", Optics Letters, 1995, vol. 20, no. 16, pp. 1716-1718, https://doi.org/10.1364/OL.20.001716.
Huang et al., "Tissue characterization using terahertz pulsed imaging in reflection geometry", Physics in Medicine & Biology, 2009, First Published: Dec. 10, 2008, vol. 54, No. 1, pp. 149-160.
Jacques, "Optical properties of biological tissues: a review", Physics in Medicine & Biology, May 10, 2013, vol. 58, No. 11, pp. R37-R61.
Middendorf et al., "THz generation using extrinsic photoconductivity at 1550 nm", Optics Express, Jul. 16 2012, vol. 20, No. 15, pp. 16504-16509.
Nagatsuma et al., "Terahertz imaging based on optical coherence tomography", Photonics Research, Aug. 2014, vol. 2, No. 4, pp. B64-B69, https://doi.org/10.1364/PRJ.2.000B64.
Peter et al., "Coherent terahertz detection with a large-area photoconductive antenna", Applied Physics Letters, 2007, vol. 91, No. 081109, 3 pgs. https://doi.org/10.1063/1.2772783.
Pickwell-Macpherson, "Practical Considerations for in Vivo THz Imaging", Terahertz Science and Technology, Dec. 2010, vol. 3, No. 4, pp. 163-171.
Preu et al., "1550 nm ErAs:In(Al)GaAs large area photoconductive emitters", Applied Physics Letters, 2012, vol. 101, No. 101105, 5 pgs., https://doi.org/10.1063/1.4750244.
Preu et al., "Tunable, continuous-wave Terahertz photomixer sources and applications", Journal of Applied Physics, 2011, vol. 109, pp. 016301-1-061301-56.
Sukhotin et al., "Photomixing and photoconductor measurements on ErAs/InGaAs at 1.55 pm", Appl. Phys. Lett., vol. 82, No. 18, May 5, 2003, pp. 3116-3118.

Sun et al., "Room Temperature GaN/AlGaN Self-Mixing Terahertz Detector Enhanced by Resonant Antennas", Applied Physics Letters, American Institute of Physics, Jun. 20, 2011 (Jun. 20, 2011), vol. 98, No. 25, pp. 252103-252103.
Takayanagi et al., "High-resolution time-of-flight terahertz tomography using a femtosecond fiber laser", Optics Express, 2009, vol. 17, No. 9, pp. 7533-7539, https://doi.org/10.1364/OE.17.007533.
Tani et al., "Detection of terahertz radiation with low-temperature-grown GaAs-based photoconductive antenna using 1.55 pm probe", Applied Physics Letters, Aug. 28, 2000, vol. 77, No. 9, pp. 1396-1398, https://doi.org/10.1063/1.1289914.
Tanigawa et al., "Enhanced Responsivity in a Novel AlGaN/GaN Plasmon-Resonant Terahertz Detector Using Gate-Dipole Antenna with Parasitic Elements", Device Research Conference (DRC), 2010, IEEE, Piscataway, NJ, USA Jun. 21, 2010 (Jun. 21, 2010), pp. 167-168.
Tsuda et al., "Application of Plasmon-Resonant Microchip Emitters to Broadband Terahertz Spectroscopic Measurement", Journal of the Optical Society of America B, Sep. 1, 2009 (Sep. 1, 2009), vol. 26, No. 9, p. A52, 6 total pgs.
Wallace et al., "Terahertz pulsed imaging and spectroscopy for biomedical and pharmaceutical applications", Faraday Discussions, 2004, First Published: Oct. 31, 2003 vol. 126, pp. 255-263.
Wallace et al., "Three-dimensional imaging of optically opaque materials using nonionizing terahertz radiation", Journal of the Optical Society of America A, 2008, vol. 25, no. 12, pp. 3120-3133, https://doi.org/10.1364/JOSAA.25.003120.
Wang et al., "Noise Analysis of Photoconductive Terahertz Detectors", Journal of Infrared, Millimeter, and Terahertz Waves, Jul. 11, 2013, vol. 34, pp. 519-528.
Wang et al., "Plasmonic photoconductive detectors for enhanced terahertz detection sensitivity", Optical Society of America, Opt. Express, vol. 21, No. 14, Jul. 15, 2013, pp. 17221-17227.
Yang et al., "7.5% Optical-to-Terahertz Conversion Efficiency Offered by Photoconductive Emitters Wth Three-Dimensional Plasmonic Contact Electrodes", IEEE Transactions on Terahertz Science and Technology, Sep. 2014, First Published: Aug. 6, 2014, vol. 4, No. 5, pp. 575-581, DOI: 10.1109/TTHZ.2014.2342505.
Yang et al., "Enhanced light—matter interaction at nanoscale by utilizing high-aspect-ratio metallic gratings", Optics Letters, 2013, vol. 38, No. 18, pp. 36773679, https://doi.org/10.1364/OL.38.003677.
Yardimci et al., "Large Area Plasmonic Photoconductive Emitters for Generating High Power Broadband Terahertz Radiation", Frontiers in Optics, Tucson, Arizona United States, Oct. 19-23, 2014, https://doi.org/10.1364/FIO.2014.FTh3E.5.
Yardimci et al., "Plasmonics enhanced terahertz radiation from large area photoconductive emitters", 2014 IEEE Photonics Conference, San Diego, CA, USA, Oct. 12-16, 2014, pp. 326-327, DOI: 10.1109/IPCon.2014.6995376.
Yu et al., "The potential of terahertz imaging for cancer diagnosis: A review of investigations to date", Quantitative Imaging in Medicine and Surgery, Mar. 2012, vol. 2, No. 1, pp. 33-45, doi: 10.3978/j.issn.2223-4292.2012.01.04.

* cited by examiner

TERAHERTZ ENDOSCOPY THROUGH LASER-DRIVEN TERAHERTZ SOURCES AND DETECTORS

CROSS REFERENCE TO RELATED APPLICATIONS

This application claims priority to U.S. Provisional Application Ser. No. 62/579,676, entitled "Systems and Methods For Terahertz Imaging" to Mona Jarrahi, filed Oct. 31, 2017 and is a national stage of PCT Patent Application No. PCT/US2016/034704, entitled "Terahertz Endoscopy through Laser-Driven Terahertz Sources and Detectors" to Mona Jarrahi, filed May 27, 2016, which claims priority to U.S. Provisional Application Ser. No. 62/167,201, entitled "Terahertz Endoscopy Through Laser-Driven Terahertz Sources and Detectors" to Mona Jarrahi, filed May 27, 2015, the disclosures of which are incorporated by reference herein in their entirety.

STATEMENT OF FEDERALLY SPONSORED RESEARCH

This invention was made with government support under Grant Number N00014-14-1-0573, awarded by the Office of Naval Research. The government has certain rights in the invention.

FIELD OF THE INVENTION

The present invention generally relates to endoscopy and more specifically to systems and methods for terahertz ($10^{12}$ Hz) endoscopy through laser-driven terahertz sources and detectors.

BACKGROUND

Endoscopy involves looking inside a body using an endoscope (an instrument that can be used to examine the interior of an organ or cavity within the body). Endoscopes can be inserted directly into an organ or cavity as opposed to other imaging devices that generate images with data collected from outside of the body. Typically, an endoscope can include a rigid or flexible tube, an illumination source, and an optical imaging system for collecting image data. Although modern endoscopy is typically discussed in the context of medical procedures, it can also be utilized for non-medical procedures such as (but not limited to) bomb disposal and surveillance to name a few.

SUMMARY OF THE INVENTION

Systems and methods for application identification in accordance with embodiments of the invention are disclosed. In one embodiment, a terahertz imaging system for endoscopy is provided. The terahertz imaging system includes a terahertz imager configured to receive terahertz image data that itself includes at least one terahertz source configured to generate terahertz radiation, wherein each of the at least one terahertz source has an active area having at least one plasmonic contact electrode that can be illuminated by optical pump beams to generate the terahertz radiation, at least one terahertz detector configured to receive terahertz field data, wherein each of the at least one terahertz detector has an active area having at least one plasmonic contact electrode that can be illuminated by optical pump beams to induce an output proportional to the received terahertz field, and the at least one terahertz source and detector are arranged in an array.

In a further embodiment, the terahertz imaging system includes an optical light source configured to illuminate at least one target. In another embodiment, an optical camera configured to receive optical image data related to the illuminate target.

In a still further embodiment, a laser source configured to pump the at least one terahertz source and detector using femtosecond optical beams. In still another embodiment, the laser source is a phase-modulated dual-laser-synchronized control femtosecond laser.

In a yet further embodiment, the at least one terahertz source and detector are fabricated on an InGaAs substrate.

In yet another embodiment, the at least one terahertz source and detector are fabricated on a GaAs substrate.

In a further embodiment again, the terahertz imaging system includes an electrical input to the at least one terahertz source to generate a bias voltage.

In another embodiment again, the terahertz imaging system includes

In a further additional embodiment, an electrical output from the at least one terahertz detector configured to collect the output from the at least one terahertz detector.

In another additional embodiment, the at least one terahertz source and detector are mounted on a silicon lens.

In a still yet further embodiment, the at least one terahertz source and detector are arranged in an array such that each terahertz detector is surrounded by four terahertz sources symmetrically. In still yet another embodiment, image data is collected simultaneously from the optical camera and the terahertz imager. In a still further embodiment again, at least one panoramic image is generated from the optical image data and terahertz image data using cross registration algorithms to map the optical image data to the terahertz image data. In still another embodiment again, the at least one terahertz source and detector are compatible with 1550 nanometer optical wavelengths. In a still further additional embodiment, the at least one terahertz source and detector are compatible with at least one of: 800 nanometer optical wavelengths and 1000 nanometer optical wavelengths.

In still another additional embodiment, the terahertz imaging system further includes at least one optical lens.

In another embodiment, a terahertz imaging system for endoscopy is provided. The terahertz imaging system includes a terahertz imager configured to receive terahertz image data itself including: at least one terahertz source configured to generate terahertz radiation, where each of the at least one terahertz source has an active area that can be illuminated by optical pump beams to generate the terahertz radiation, at least one rotating element configured to reflect the generated terahertz radiation across scanned material, at least one terahertz detector configured to receive terahertz radiation reflected by the at least one rotating element, wherein each of the at least one terahertz detector has an active area that can be illuminated by optical pump beams to induce an output proportional to the received terahertz field, and the at least one terahertz source, at least one rotating element, and at least one terahertz detector are arranged in an catheter.

In yet another embodiment again, the at least one rotating element is a mirror mounted at a particular angle on a micromotor within the catheter. In yet another additional embodiment, the micromotor can rotate the at least one rotating element during reflection of the generated terahertz radiation across the scanned material.

In a further additional embodiment again, the at least one terahertz source has at least one plasmonic contact electrode, and the at least one terahertz detector has at least one plasmonic contact electrode.

DETAILED DESCRIPTION OF THE DRAWINGS

Turning now to the drawings, systems and methods for terahertz endoscopy utilizing terahertz sources and detectors in accordance with embodiments of the invention are disclosed. In many embodiments, the systems and methods can include a so-called terahertz imager configured to illuminate and receive terahertz image data using at least one terahertz source and detector as further described below. In a variety of embodiments, the at least one terahertz source and detector can be arranged in a large area array as further described below. In several embodiments, the terahertz sources and detectors can utilize plasmonic contact electrodes and be illuminated using femtosecond ($10^{-15}$ second) lasers as further discussed below. In various embodiments, terahertz sources and detectors can be fabricated on any substrate that can absorb photons in various operating wavelength ranges including (but not limited to) ErAs:InGaAs, GaAs, InGaAs, Ge, InP, graphene, and GaN substrates to name a few. Although specific embodiments utilizing a ErAs:InGaAs substrate are discussed below, one of ordinary skill in the art would appreciate that any of a variety of substrates as appropriate to the specific application can be utilized in accordance with embodiments of the invention.

In addition, the terahertz sources and detectors can be mounted on an optical lens includes (but not limited to) silicon lens. In a variety of embodiments, the systems and methods can also incorporate an optical light source and optical camera to capture optical image data. The optical image data and terahertz image data can be combined to further enhance the ability to generate images for diagnostics and other endoscopic purposes.

In some embodiments, the systems and methods can include terahertz imaging systems configured for compatibility with various endoscopes allowing for terahertz imaging of internal organs of living species including (but not limited to) humans. Typically, the terahertz waves can produce lower energy and reduce ionization hazards for human tissues compared to typical medical imaging systems that utilize shorter wavelength waves. In several embodiments, the terahertz waves can experience less scattering from biological tissue compared to optical waves due to their longer wavelengths making it possible to "see" deeper into various biological tissue types. Further, several absorption lines of water are typically found in the terahertz frequency spectrum, making terahertz waves a very powerful means for distinguishing between tissues with different hydration levels which can be useful for diagnostics purposes. Thus, terahertz imaging can be effective in offering image contrasts for applications including (but not limited to) identifying cancerous tissues, assessment of burn injuries, in-vivo imaging, and diagnostics for the upper and lower gastrointestinal and respiratory tract, to name a few.

Figure 1A:
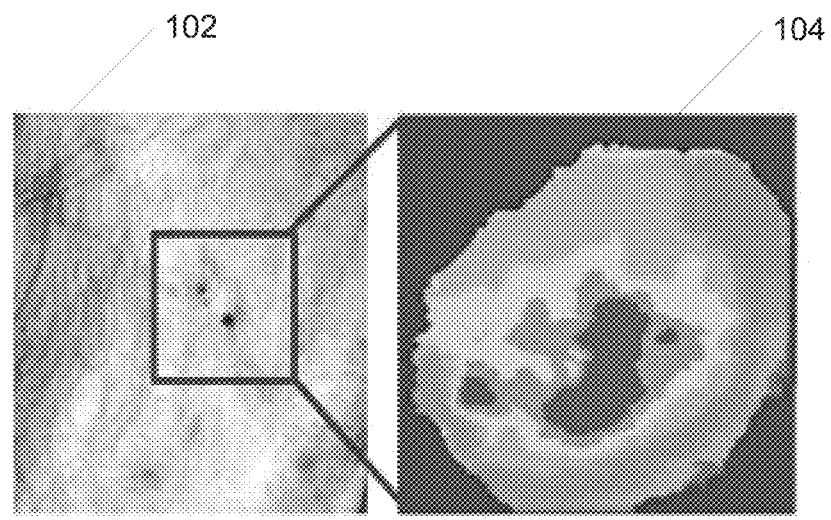
FIG. 1a illustrates an optical and terahertz image of a tissue with Basal Cell Carcinoma in accordance with an embodiment of the invention.
Figure 1B:
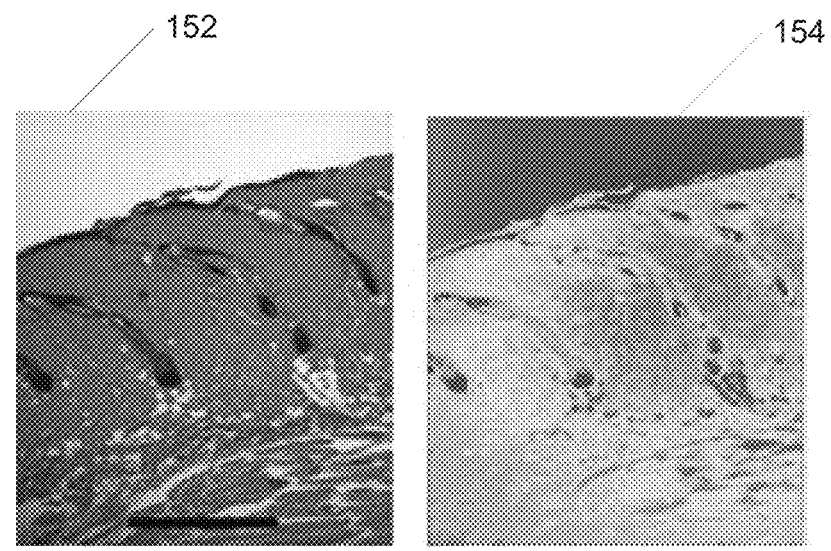
FIG. 1b illustrates an optical and terahertz image of a skin tissue with third-degree burn in accordance with an embodiment of the invention.

Terahertz imaging offers image contrasts not typically seen using other imaging techniques such as standard optical methods. An optical and a terahertz based images of a tissue with Basal Cell Carcinoma in accordance with an embodiment of the invention is shown in FIG. 1a. The images 100 show an optical based image 102 side-by-side with a terahertz based image 104. In addition, optical and terahertz based images of a skin tissue with third-degree burn in accordance with an embodiment of the invention is shown in FIG. 1b. The images 150 show an optical based image 152 side-by-side with a terahertz based image 154. In both FIGS. 1a and 1b, the images generated utilizing terahertz based imaging show stronger contrasts for the cancerous and damaged tissue, respectively. Although specific images illustrating superior image contrasts using terahertz based imaging systems are discussed above with respect to FIGS. 1a-b, any of a variety of images and terahertz based imaging systems as appropriate to the requirements of a specific application can be utilized in accordance with embodiments of the invention. Systems and methods for terahertz endoscopy utilizing terahertz sources and detectors in accordance with embodiments of the invention are discussed further below.

Pulsed Terahertz Imaging Systems for Endoscopy

Figure 2A:
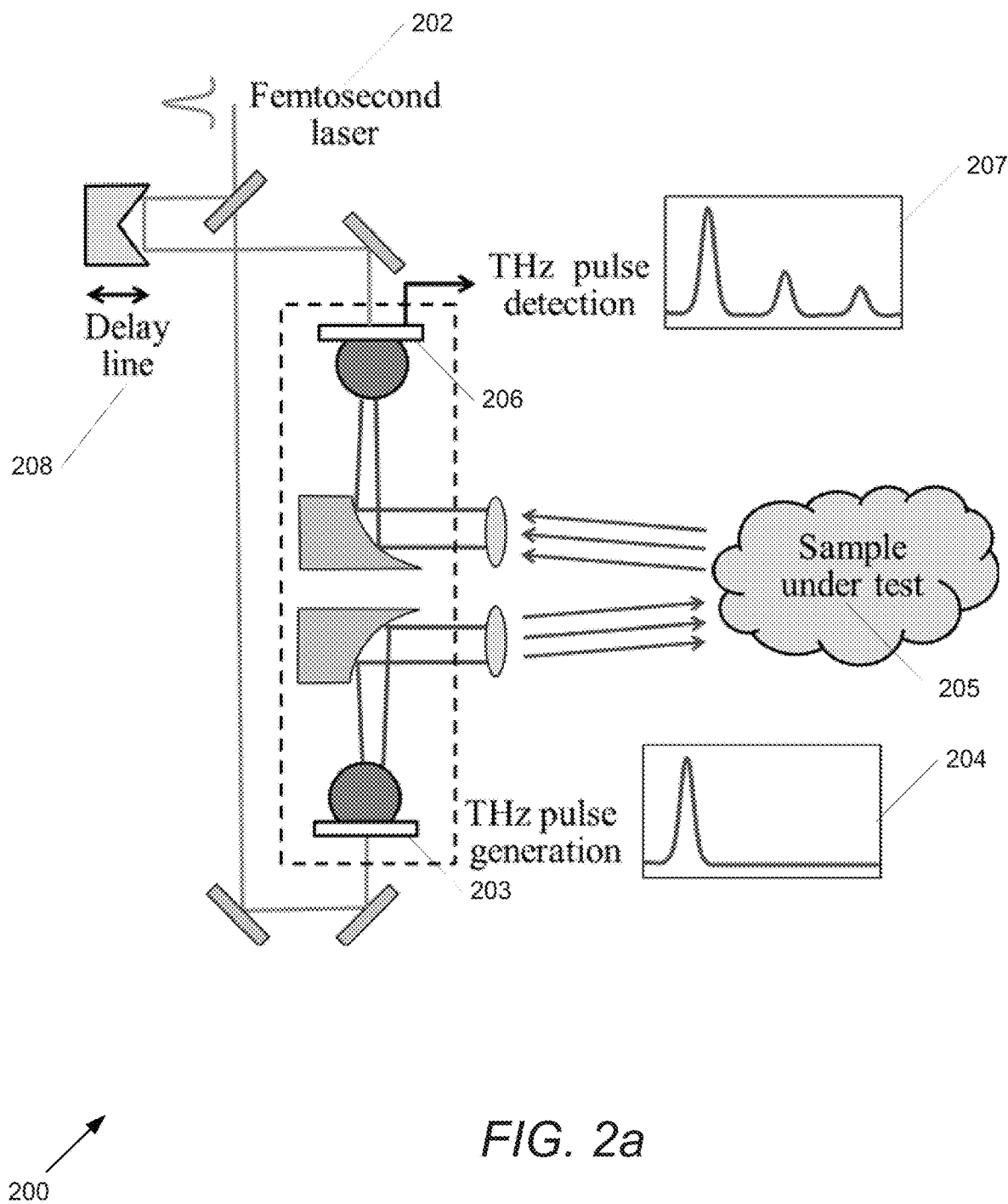
FIG. 2a is a schematic diagram of a terahertz imaging system utilizing a single femtosecond laser in accordance with an embodiment of the invention.

Among various techniques for non-contact three-dimensional terahertz imaging, pulsed imaging systems can be utilized for resolving images with high depth resolution. Typically, non-contact three-dimensional terahertz imaging can leverage the availability of femtosecond optical lasers that can generate sub-picosecond ($10^{12}$ second) electromagnetic pulses through photoconduction or nonlinear optical processes. A schematic diagram illustrating a pulsed terahertz imaging system in reflection mode is shown in FIG. 2a. In many embodiments, the pulsed terahertz imaging system 200 can be more compatible with medical imaging applications compared to various comparable imaging systems in transmission mode. The pulsed terahertz imaging system illustrated in FIG. 2a can be based on photoconductive terahertz sources and detectors as further discussed below. In various embodiments, nonlinear optical processes can also be used for terahertz pulse generation and/or detection.

In several embodiments, a femtosecond optical pulse train from a mode-locked laser 202 can be incident on a photoconductive terahertz source 203 to generate a sub-picosecond terahertz pulse train 204 (typically with frequency components within 0.1-4 THz), which can then be focused onto a specific spot on a sample under test 205. In many embodiments, a terahertz signal is reflected from the test sample and can be detected utilizing a photoconductive terahertz detector 206 where the detector can be probed by a copy of the femtosecond optical pump pulse train 207. In various embodiments, a controllable optical delay line 208 can allow for adjusting the time-delay between the pump and probe optical beams and, thus, the reflected signal from the sample can be measured in the time domain. In many embodiments, depth profile of the specific scanned spot on the sample can be resolved by measuring the amplitude and timing of the reflected signal. By scanning the sub-picosecond terahertz pulse train across other spots on the sample under test in the lateral direction and resolving the depth profile of each scanned spot, a three-dimensional image of the sample can be resolved.

Typically, for non-contact pulsed terahertz imaging systems, lateral resolution of the resolved image can be limited by diffraction and, thus, is determined based upon the effective wavelength of the incident terahertz beam inside the imaged object and numerical aperture of the utilized lenses. In many embodiments, the depth resolution of the resolved image can be determined based upon the pulse width of the incident terahertz pulses inside the imaged object, which can be estimated as $\sim c \cdot \Delta t/(2n)$, where c is the speed of light, $\Delta t$ is the pulse width of the incident terahertz pulse on the object, and n is the effective refractive index of the object at terahertz frequencies. Therefore, by considering the effective index of biological tissues at terahertz frequencies, a depth resolution of less than 0.1 mm can be expected for the pulsed imaging system with sub-picosecond terahertz pulses for medical imaging applications. In many embodiments, this depth resolution is much better than what can be offered by other terahertz imaging systems based on continuous-wave terahertz sources, which are limited by the bandwidth and frequency of high power continuous-wave terahertz sources. While pulsed terahertz imaging systems can offer superior depth resolutions compared to other terahertz imaging systems, there can be a number of factors that can still limit the scope and potential use of the pulsed terahertz imaging systems for practical medical imaging applications.

A first limitation concerns the detectable penetration depth of the incident terahertz beam (maximum depth of tissue that can be imaged) which can be limited by attenuation of the imaged sample and the signal-to-noise ratio of the terahertz imaging system. While the attenuation of various types of biological tissue are bound by their structure and water content, the output terahertz power of photoconductive terahertz sources and sensitivity of photoconductive terahertz detectors (or any other type of pulsed terahertz source and detector employed in an imaging system) can be key factors for setting the maximum detectable penetration depth of the imaging system. In spite of the great promise of pulsed imaging systems for offering high depth resolutions, some of the major challenges in realizing terahertz imaging systems for various medical diagnostics applications can include the relatively low radiation power of existing terahertz radiation sources and low detection sensitivity of existing terahertz detectors that limit the maximum detectable depth of the imaging system.

A second limitation concerns image acquisition time, which can be limited by the axial scan time of the depth profile of each specific spot of the sample under test as well as the lateral scan time of all the spots across the sample. The axial scan time of the depth profile of each specific spot of the sample can be limited by the mechanical delay lines 208 utilized in a pulsed imaging system as illustrated in FIG. 2a. However, in many embodiments, the axial scan times can be significantly reduced by use of phase-modulated dual-laser-synchronized control technology. For example, Advantest America, Inc. located in San Jose has offered a two-channel femtosecond laser system (50 fs pulses at 1550 nm) with a synchronized and controllable phase modulation between the two laser channels without a mechanical optical delay line, enabling axial scanning speeds of ~1 msec/scan. It should also be noted that multiple scans can be used for capturing the depth profile of each specific spot of the sample with higher signal-to-noise ratios, resulting in a tradeoff between image quality and acquisition time. Although the axial scan times can be significantly reduced by utilizing imaging systems with higher signal-to-noise ratio levels, the main limitation for achieving fast image acquisition rates can be that the lateral scan time of all the spots across the sample under test is limited by the mechanical scanning processes used in pulsed terahertz imaging systems.

Figure 2B:
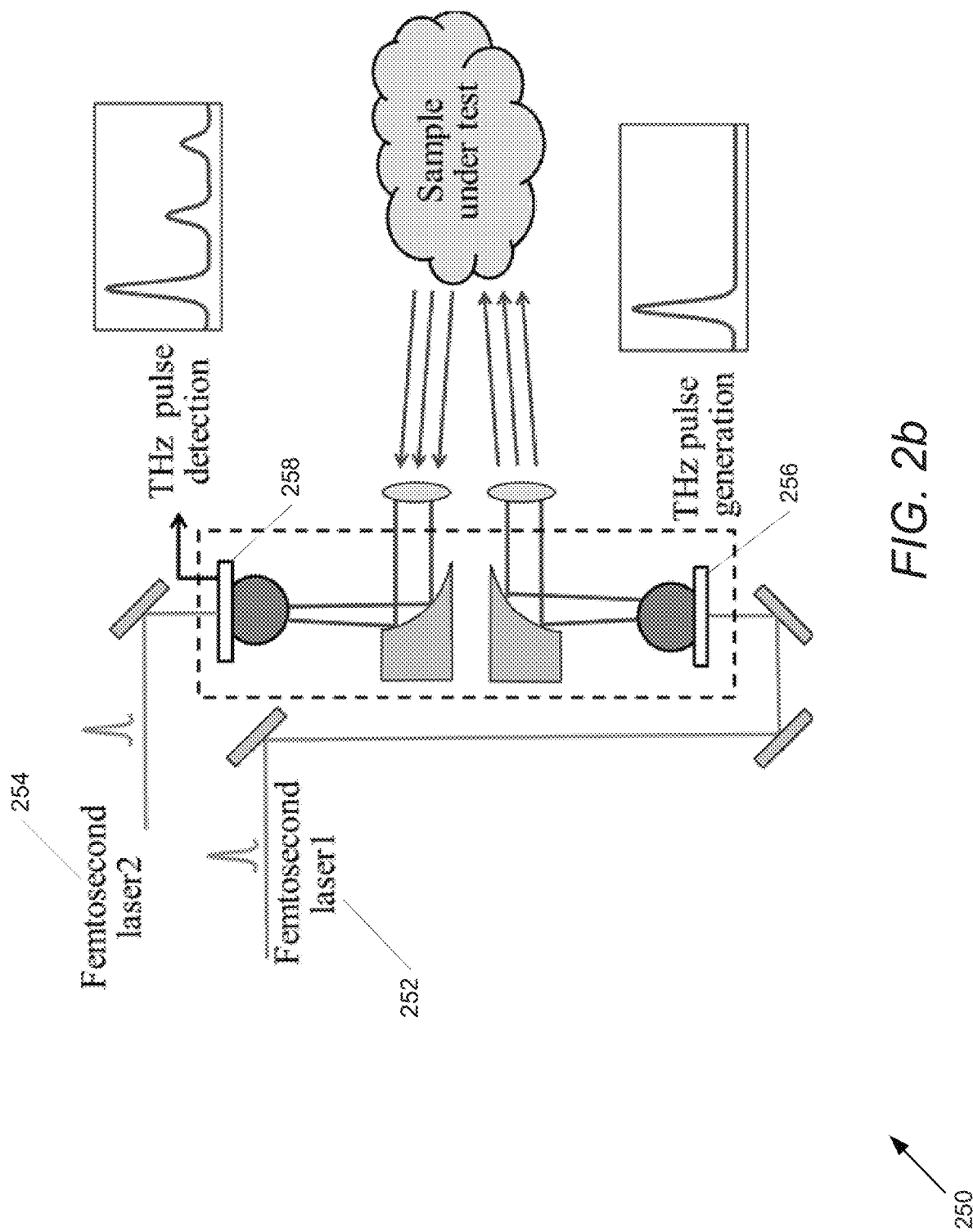
FIG. 2b is a schematic diagram of a terahertz imaging system utilizing a synchronized phase-modulated dual femtosecond laser in accordance with an embodiment of the invention.

A schematic diagram of a terahertz imaging system utilizing a synchronized phase-modulated dual femtosecond laser in accordance with an embodiment of the invention is shown in FIG. 2b. The terahertz imaging system 250 can include a phase-modulated dual-laser-synchronized control femtosecond laser comprising a first femtosecond laser 252 and a second femtosecond laser 254 that can be utilized for pumping plasmonic photoconductive terahertz sources 256 and detectors 258 to significantly reduce the axial scan time. In a variety of embodiments, the terahertz imaging system can be compatible with commercially available endoscopes such as (but not limited to) those produced by Karl Storz Endoscopy Inc. to be able to explore new range of in-vivo medical imaging applications for diagnostics purposes. In many embodiments, the large area plasmonic photoconductive sources and detectors can be compatible with 700-1550 nm optical wavelengths (including but not limited to 800, 1000, or 1550 nm) at which low dispersion optical fibers are available for maintaining the pulse width of the femtosecond pump beams over a fiber length of several meters. Although specific embodiments utilizing a 1550 nm optical wavelength are discussed below, one of ordinary skill in the art would appreciate that any of a variety of optical wavelengths as appropriate to the specific application can be utilized in accordance with embodiments of the invention. It should be appreciated that the embodiments of the invention as illustrated discuss utilizing 1550 nm as way of example, but could be applied using other optical wavelengths. Further, optical wavelengths can sometimes be expressed in microns (i.e. 1 micron=1000 nm).

Although specific pulsed terahertz imaging system utilizing femtosecond lasers are discussed above with respect to FIGS. 2a-b, any of a variety of pulsed terahertz imaging systems incorporating femtosecond lasers as appropriate to the requirements of a specific application can be utilized in accordance with embodiments of the invention. Imaging systems based on an array of large area plasmonic terahertz sources and detectors in accordance with embodiments of the invention are discussed further below.

Pulsed Terahertz Imaging Systems Based on Arrays

A pulsed terahertz imaging system based on an array of large area plasmonic photoconductive terahertz sources and detectors can enable non-contact three dimensional imaging with significantly larger detectable depth and faster acquisition rates. In many embodiments, the pulsed terahertz imaging system can be based on a two-dimensional array of large area plasmonic photoconductive terahertz sources and detectors compatible with commercially available endoscopes.

In various embodiments, the large area plasmonic photoconductive sources and detectors can be effective in enhancing the output power of terahertz sources, detection sensitivity of terahertz detectors and thus, signal-to-noise ratio of the imaging system by several orders of magnitude, enabling significantly larger detectable depths for the imaging system. Further, the two-dimensional array of plasmonic photoconductive sources and detectors can significantly increase the image acquisition rate by reducing the lateral scan time. Moreover, in several embodiments, an image processing technique can be utilized to offer in-vivo terahertz imaging with large field of view. Since the overall size of the two dimensional array of plasmonic photoconductive sources and detectors is often limited by the endoscope tip size constraints and the dimension of each detector pixel would be comparable with the diffraction limit, the total number of image pixels can be limited to 3×3 in many implementations. In order to extend the overall field of view and resolve images with effectively larger number of pixels, an image processing technique can be utilized that processes the image data from the terahertz imager with relatively small number of pixels together with the higher resolution optical images captured by an optical camera (available at the tip of the endoscope) while moving the endoscope tip. In various embodiments, panoramic images can be produced from the optical and terahertz image data using cross registration algorithms to map the high resolution optical images to the terahertz images, which could be very beneficial for diagnostics purposes.

As discussed further below, the terahertz imaging systems can be expected to offer more than 3 mm detectable depth in biological tissue (can penetrate deeper depending on the tissue type) with depth resolution of ~30 um, sub-millimeter lateral resolution and image acquisition time of ~1 msec for each 3×3 pixels. Such a system could have a transformative impact on the scope and potential use of terahertz imaging for a variety of tomography and hydration/inflammation measurements with potential application including (but not limited to) the upper and lower gastrointestinal and respiratory tract.

Figure 3:
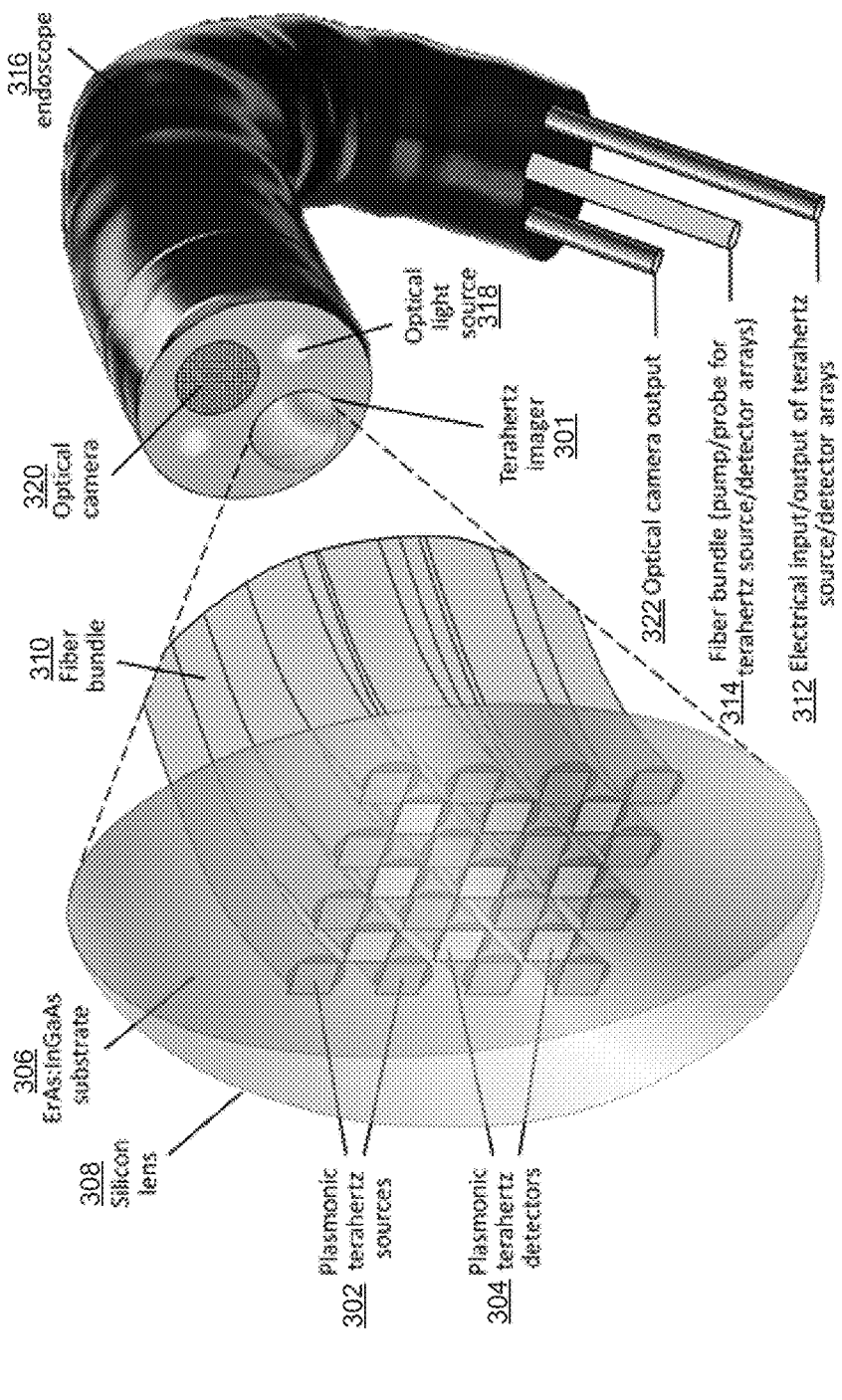
FIG. 3 is a schematic diagram of a terahertz imaging system in accordance with an embodiment of the invention.

A schematic diagram of a terahertz imaging system utilizing an array of large area plasmonic terahertz sources and detectors in accordance with an embodiment of the invention is illustrated in FIG. 3. The imaging system 300 can comprise a terahertz imager 301 comprising an array of large area plasmonic terahertz sources 302 and detectors 304 fabricated on an ErAs:InGaAs substrate 306, mounted on a silicon lens 308, and pumped by femtosecond optical beams from a phase-modulated dual-laser-synchronized control femtosecond laser ($\lambda \approx 1550$ nm). Although a 1550 nm optical wavelength is illustrated, any of a variety of wavelengths as appropriate to the requirements of a specific application can be utilized in accordance with embodiments of the invention. Here, the 1550 nm wavelength is selected since the Advantest phase-modulated dual-femtosecond-laser system operates at 1550 nm wavelength range and the availability of a large number of fiber optics components for coupling laser light to the arrays of terahertz sources and detectors.

In several embodiments, an array of polarization that maintains fiber splitters can be utilized to couple the dual laser beam into a polarization maintaining fiber bundle 310, that can be used to couple the pump and probe beams to the active area of large area plasmonic photoconductive terahertz source and detectors arrays, respectively. Further, the arrays of terahertz sources and detectors can be arranged such that each terahertz detector is surrounded by four terahertz sources symmetrically.

In various embodiments, arrays of terahertz sources and detectors, optical pump/probe fiber bundle 314, electrical input to the terahertz source arrays 312 (bias voltage of the large area plasmonic terahertz sources), and electrical output of the terahertz detector arrays 312 (output current of the large area plasmonic terahertz detectors) can be arranged and packaged to fit inside a channel of various endoscopes 316 including (but not limited to) a commercially available endoscope that can vary in size and offer an empty channel including (but not limited to) channels with a diameter varying between 2 mm to 5 mm. In several embodiments, the output of the terahertz detector can be an output current and/or an output voltage.

In various embodiments, the endoscopes can have flexibility allowing ±100 degree tilting at the tip, making it possible to capture images from the gastrointestinal and respiratory tract side walls from various angles. In many embodiments, the imaging systems can include an optical light source 318 and an optical camera 320 such as (but not limited to) a fiber bundle or CCD imager placed at the tip of the endoscope having an optical camera output 322. In various embodiments, images can be captured using the endoscope's optical camera 320 and the terahertz imager 301 (i.e. terahertz sources and detectors) simultaneously. As discussed further below, capturing an image with the endoscope's optical camera and the terahertz imager simultaneously can improve image processing at various processing stages and for cross registering the optical and terahertz images for diagnostics applications. Although specific terahertz imaging systems using an array of large area plasmonic terahertz sources and detectors are discussed above with respect to FIG. 3, any of a variety of terahertz imaging systems having an array of large area plasmonic terahertz sources and detectors as appropriate to the requirements of a specific application can be utilized in accordance with embodiments of the invention. Array of terahertz sources and detectors for terahertz imaging systems in accordance with embodiments of the invention are discussed further below.

Plasmonic Photoconductive Terahertz Sources and Detectors

As discussed above, terahertz imaging systems in accordance with embodiments of the invention can include arrays of plasmonic photoconductive terahertz sources and detectors. Typically, when the active area of a large area photoconductive source is illuminated by an optical pump beam, photo-generated electrons and holes are accelerated in opposite directions by the external bias electric field. The acceleration and separation of photo-carriers can induce a time-varying dipole moment within the device's active area which generates terahertz radiation. Similarly, when an active area of large area photoconductive detectors is illuminated by an optical pump beam, photo-generated electrons and holes can be accelerated in opposite directions by the incident terahertz field. The acceleration and separation of photo-carriers can induce a photocurrent within a device's active area proportional to the received terahertz field. Large area photoconductive sources and detectors can be suitable for the terahertz imaging system because they can offer very broad radiation bandwidth, which allows generation and detection of terahertz pulses with very narrow pulse widths, offering images with high depth resolution. Further, large area photoconductive sources and detectors can operate at higher optical pump power levels and, thus, offer higher radiation powers and higher detection sensitivities compared to other types of photoconductive terahertz sources and detectors, which can be limited by the carrier screening effect and thermal breakdown at higher optical pump powers. In addition, large area photoconductive sources and detectors typically do not need a very sensitive optical alignment due to their relatively large active areas, and thus simplifying alignment of large arrays of terahertz sources and detectors with a fiber bundle.

Figure 4:
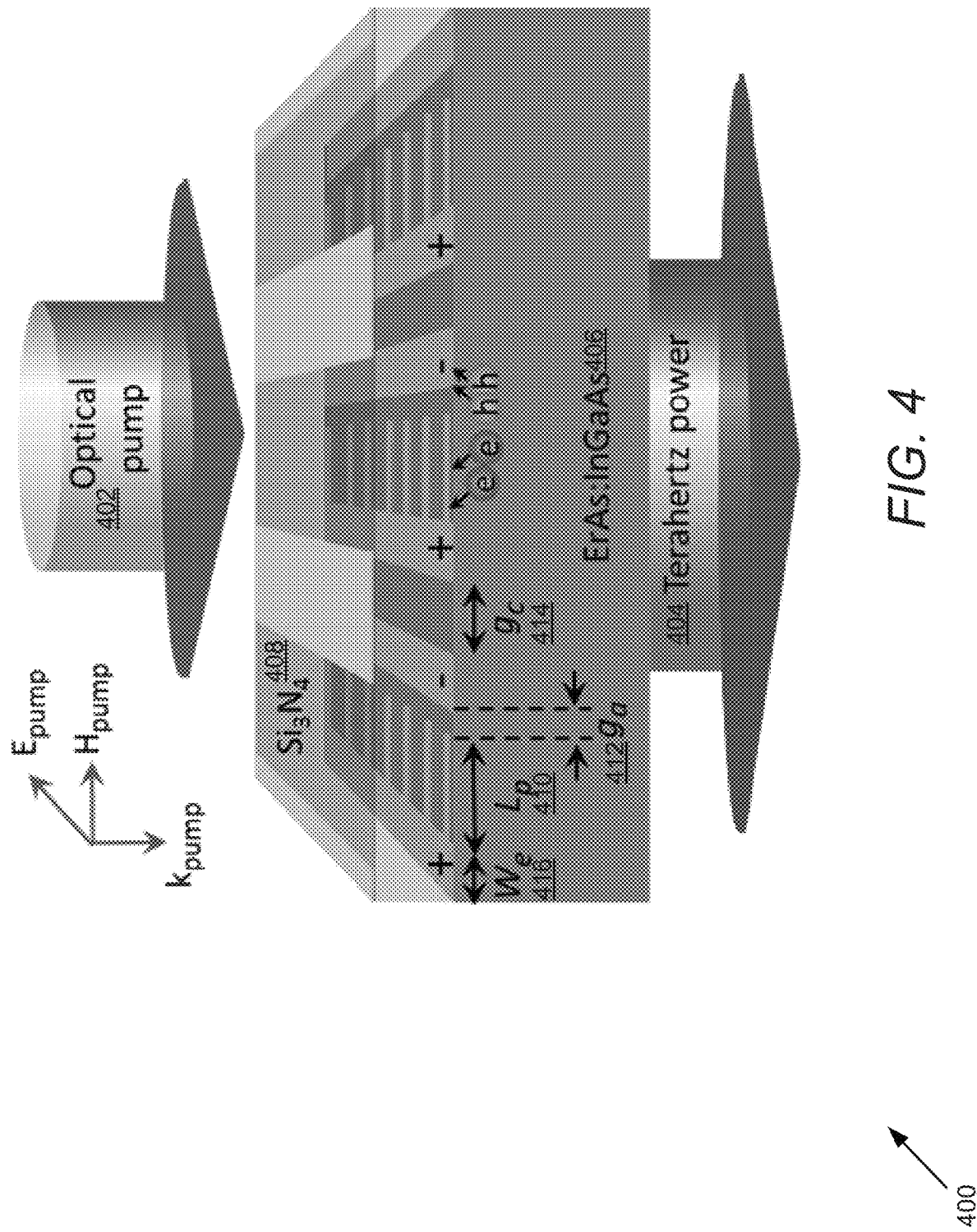
FIG. 4 is a schematic diagram of a plasmonic photoconductive terahertz source and detector in accordance with an embodiment of the invention.

Despite the promise for high power terahertz generation and high sensitivity terahertz detection (by accommodating higher optical pump power levels), the output power and detection sensitivity of large area photoconductive sources and detectors can be limited by the weak effective dipole moment and the weak photocurrent induced within the device active area, respectively. To address some of the above identified limitations, plasmonic contact electrodes can be utilized. Plasmonic contact electrodes can be effective in enhancing the radiation power and detection sensitivity of various photoconductive terahertz sources and detectors by reducing the transport path length of the photocarriers to the device contact electrodes. A schematic diagram of a large area plasmonic photoconductive source and detector and its operation concept as a terahertz source in accordance with an embodiment of the invention is illustrated in FIG. 4. The large area plasmonic photoconductive source and detector 400 incorporates plasmonic contact electrodes within the active area of large area photoconductive sources, most of the photocarriers are generated in close proximity to the contact electrodes. Therefore, the majority of the photocarriers that are drifted to the contact electrodes within a sub-picosecond time-scale. Since the contact electrodes accommodate photocurrent propagation velocities much higher than that of semiconductor substrate, a much stronger time-varying dipole moment can be induced in response to an incident optical pump 402 and, thus, greatly enhanced terahertz radiation power 404 can be achieved compared to conventional large area photoconductive sources. Similarly, incorporating plasmonic contact electrodes within the active area of large area photoconductive detectors can increase the number of the photocarriers that are drifted to the contact electrodes within a sub-picosecond time-scale in response to an incident terahertz beam. Therefore, greatly enhanced terahertz detection sensitivity can be achieved compared to conventional large area photoconductive detectors.

As illustrated in FIG. 4, the device can be fabricated on an ErAs:InGaAs substrate 406, which is used for operation at ~1550 nm optical pump wavelengths. In many embodiments, ErAs:InGaAs substrate can offer a short carrier lifetime for suppressing the low-frequency photocurrent and the relatively large substrate resistivity for maintaining a high bias electric field across the device active area and low noise operation. In various embodiments, the ErAs:InGaAs substrate can offer a carrier lifetime of 0.85 ps and substrate resistivity of ~1 KΩ.cm. In various embodiments, the device's active area can be comprised to include a set of interdigitated bias lines. In several embodiments, arrays of plasmonic contact electrode gratings can be connected to anode bias lines of the photoconductive source within every other gap between the anode and cathode bias lines. The other gaps between the anode and cathode bias lines can be shadowed by a second metal layer deposited on top of a $Si_3N_4$ antireflection coating 408 to block light transmission into the substrate and induce uni-directional dipole moment in the substrate. The geometry of the plasmonic contact electrode gratings and thickness of the $Si_3N_4$ antireflection coating can be chosen to transmit the majority of the incident optical pump photons through the plasmonic gratings into the ErAs:InGaAs substrate.

Further, various geometric parameters ($L_p$, $g_a$, $g_c$, $W_e$) can impact the performance of large area plasmonic photoconductive terahertz sources and detectors. On the hand, the length of the plasmonic gratings, $L_p$ 410, should be selected much shorter than the effective terahertz radiation wavelength to achieve a broad terahertz generation/detection bandwidth and relatively large electric field along the entire grating length for efficient drift of the photocarriers to the plasmonic gratings. On the other hand, reducing the length of the plasmonic gratings, $L_p$ 410 can reduce the percentage of the device's active area in comparison with the shadowed area and, thus, can reduce the device's quantum efficiency.

In addition, the gaps between the anode and cathode contact electrodes, $g_a$ 412 and $g_c$ 414 should be selected large enough to prevent electrical breakdown when applying bias voltages for efficient drift of photocarriers along the entire grating length. However, increasing the cathode contact electrodes, $g_a$ 412 and $g_c$ 414 can reduce the percentage of the device's active area in comparison with the shadowed area and, thus, can reduce the device's quantum efficiency.

Also, the width of the bias electrodes, $W_e$, 416 should be large enough to accommodate the induced photocurrent during device operation (especially during operation as a terahertz source, when the induced photocurrent can be considerable). In the meantime, increasing the bias electrodes, $W_e$, 416 can reduce the percentage of the device active area in comparison with the shadowed area and, thus, can reduce the device's quantum efficiency. Additionally, the geometric parameters ($L_p$, $g_a$, $g_c$, $W_e$) can determine the overall device resistance, which can directly impact the noise floor of the radiated terahertz beam and detected terahertz signal. Thus, the impact of each geometric parameter can be readily investigated by one of ordinary skill in the art and optimum device geometry as appropriate to the requirements of a specific application of large area plasmonic photoconductive sources and detectors can be determined and utilized in accordance with embodiments of the invention.

Figure 5:
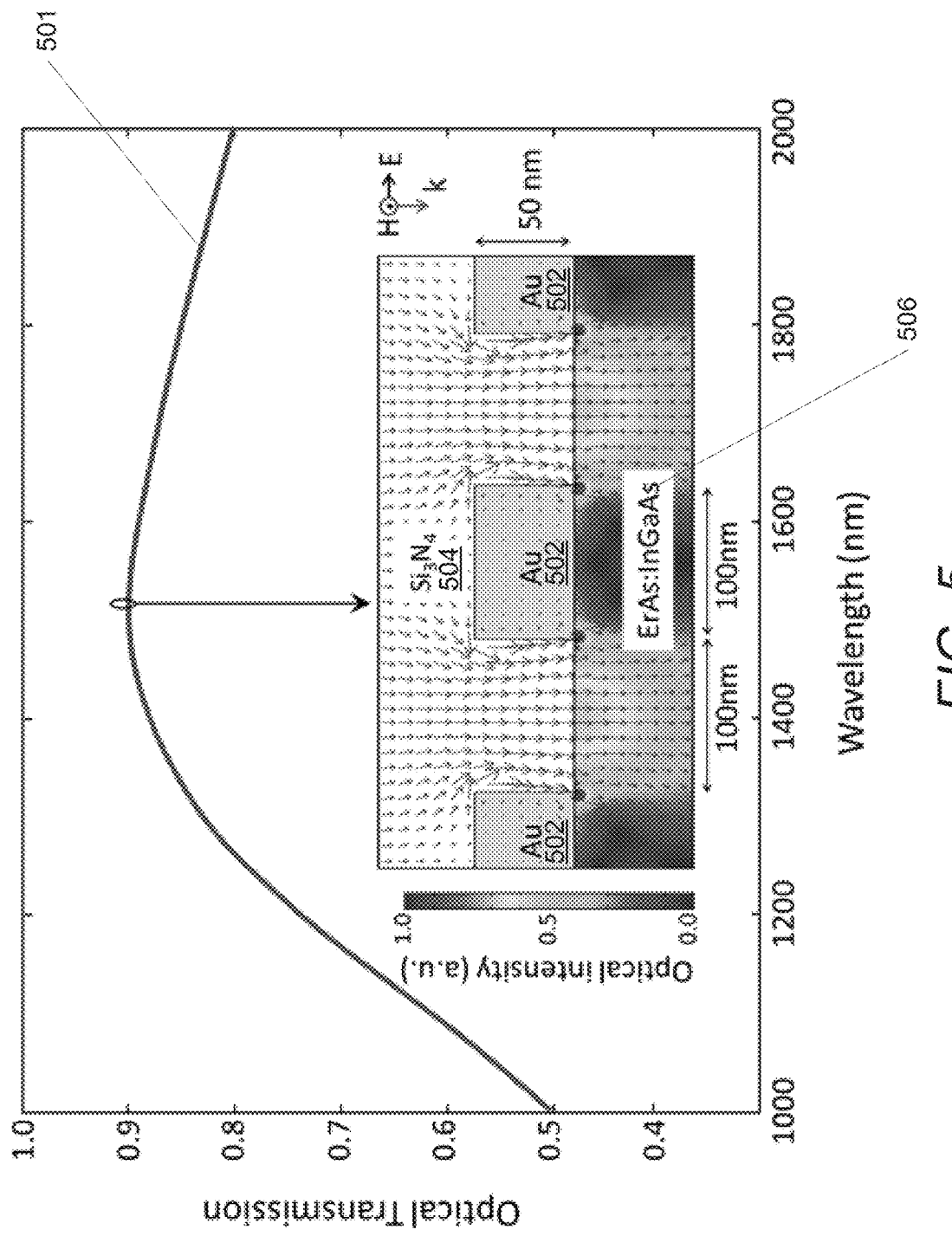
FIG. 5 illustrates a grating design along with a graph illustrating power transmission of a transverse-magnetic (TM) polarized optical beam in accordance with an embodiment of the invention.

In many embodiments, a finite-element solver (COMSOL) can be used to design the plasmonic contact electrode gratings. A grating design for a large area plasmonic photoconductive sources and detectors along with a graph illustrating power transmission of a transverse-magnetic (TM) polarized optical beam in accordance with an embodiment of the invention is illustrated in FIG. 5. The graph 501 illustrates power transmission of a TM polarized optical beam as a function of wavelength. In many embodiments, the grating design includes sources and detectors that can comprise Au gratings 502 with a 200 nm pitch, 100 nm metal width, and 50 nm metal height and a 250 nm thick $Si_3N_4$ antireflection coating 504, offering 90% optical transmission into the ErAs:InGaAs substrate 506 at 1550 nm pump wavelength. Since transmission of the incident optical pump into the substrate is through excitation of surface plasmon waves and through 100 nm gaps between the plasmonic grating fingers, a large portion of the photocarriers are generated in close proximity to the plasmonic gratings. Therefore, a large portion of the photo-generated electrons are drifted to the plasmonic gratings (anode contact electrodes) within a sub-picosecond timescale and radiate through the effective Hertzian dipole formed by the plasmonic gratings.

In various embodiments, the photocurrent propagation velocity along plasmonic gratings is not limited by the carrier scattering inside the semiconductor substrate lattice. Therefore, the Hertzian dipole antennas formed by the plasmonic gratings can offer significantly higher radiation resistance and better impedance matching to free space compared with the radiating dipole induced within the semiconductor substrate of conventional large area photoconductive sources. Similarly, the use of plasmonic contact electrodes within the active area of large area photoconductive detectors can increase the induced ultrafast photocurrent in response to an incident terahertz radiation significantly. Therefore, greatly enhanced terahertz detection sensitivity can be achieved compared to typical large area photoconductive detectors. Although specific arrays of plasmonic photoconductive terahertz sources and detectors are discussed above with respect to FIGS. 4-5, any of a variety of arrays of plasmonic photoconductive terahertz sources and detectors as appropriate to the requirements of a specific application can be utilized in accordance with embodiments of the invention. Design considerations and testing results of large area plasmonic photoconductive terahertz sources and detectors in accordance with embodiments of the invention are discussed further below.

Design Considerations and Test Data

In many embodiments, designs for the large area plasmonic photoconductive sources should maximize the optical-to-terahertz conversion efficiency and radiation power as well as the terahertz radiation bandwidth and the designs for the large area plasmonic photoconductive detectors should maximize the detection sensitivity and the terahertz detection bandwidth. In a variety of embodiments, high-aspect ratio plasmonic contact electrode gratings can be utilized for plasmonic contact electrodes in accordance with embodiments of the invention. Typically, the use of high-aspect ratio plasmonic electrodes can enhance the number of the photocarriers in close proximity to the plasmonic contact electrodes further and, thus, can offer higher terahertz radiation power levels and detection sensitivities for large area plasmonic photoconductive sources and detectors.

A pulsed terahertz radiation power levels from a 1×1 mm² large area plasmonic photoconductive terahertz source operating at 800 nm optical pump wavelength range has been achieved using device concepts similar to the design for the terahertz imaging system as illustrated in FIG. 4. In many embodiments, the device can be fabricated on a semi-insulating (SI) GaAs substrate and the geometry of the plasmonic contact electrode gratings optimized for operation at 800 nm optical wavelengths. In many embodiments, the fabrication process can start with patterning the plasmonic contact electrodes using electron-beam lithography, followed by 5/45 nm Ti/Au deposition and liftoff. An optical lithography step with a bi-layer photoresist can be used to pattern the bias lines, which can be followed by 50/550 nm Ti/Au deposition and liftoff. A $Si_3N_4$ anti-reflection coating can be deposited using plasma-enhanced chemical vapor deposition (PECVD). Typically, the shadow metal is patterned next through optical lithography, followed by 10/90 nm Ti/Au deposition and liftoff. The contact bias can be patterned using optical lithography and opened by etching the $Si_3N_4$ layer using reactive ion etching (RIE). The device can be placed on a silicon lens and an optical rotation mount to adjust the polarization of the optical pump with respect to the plasmonic gratings.

Figure 6A:
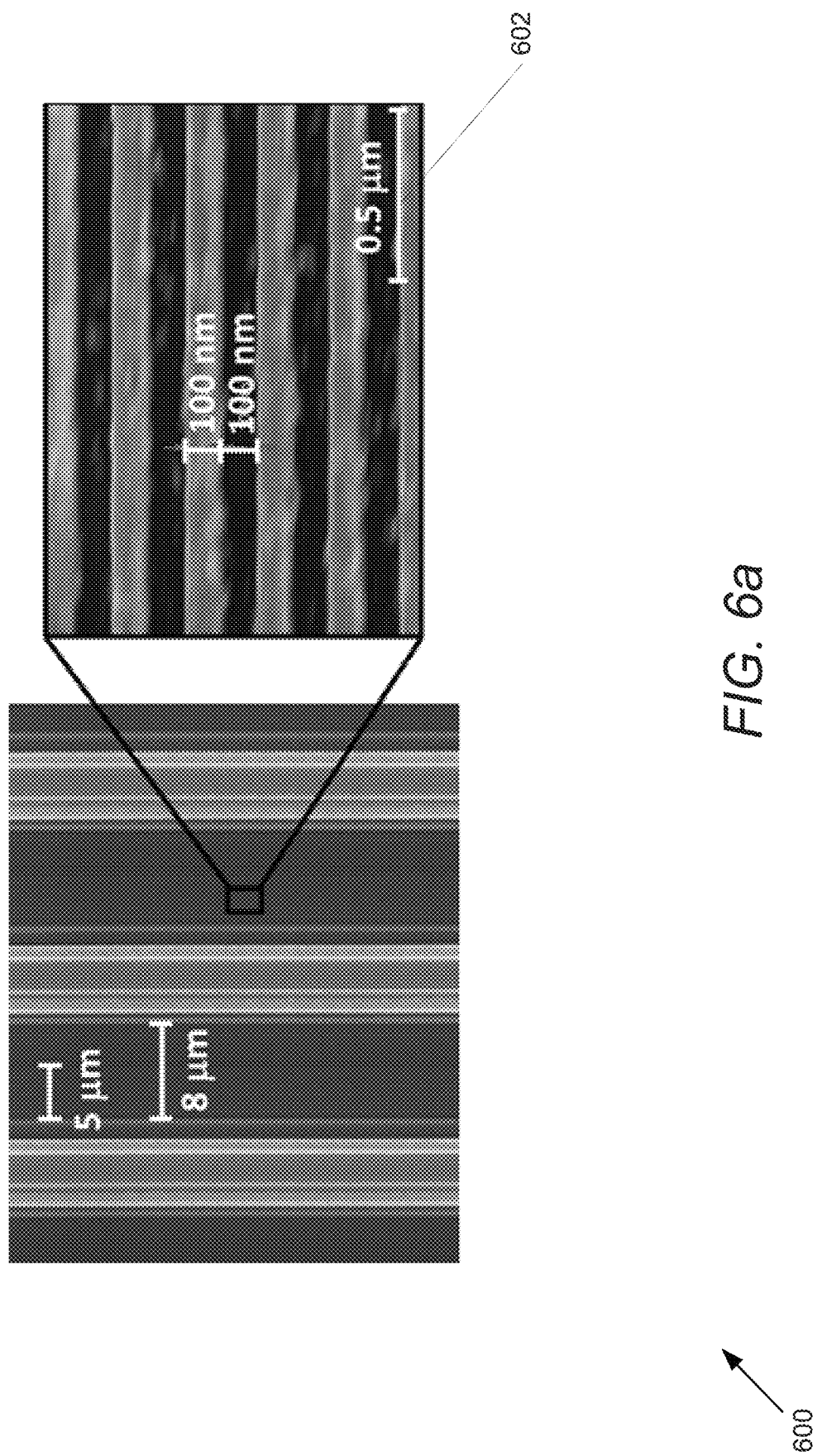
FIG. 6a illustrates a scanning electron microscope (SEM) image of a plasmonic photoconductive source in accordance with an embodiment of the invention.
Figure 6B:
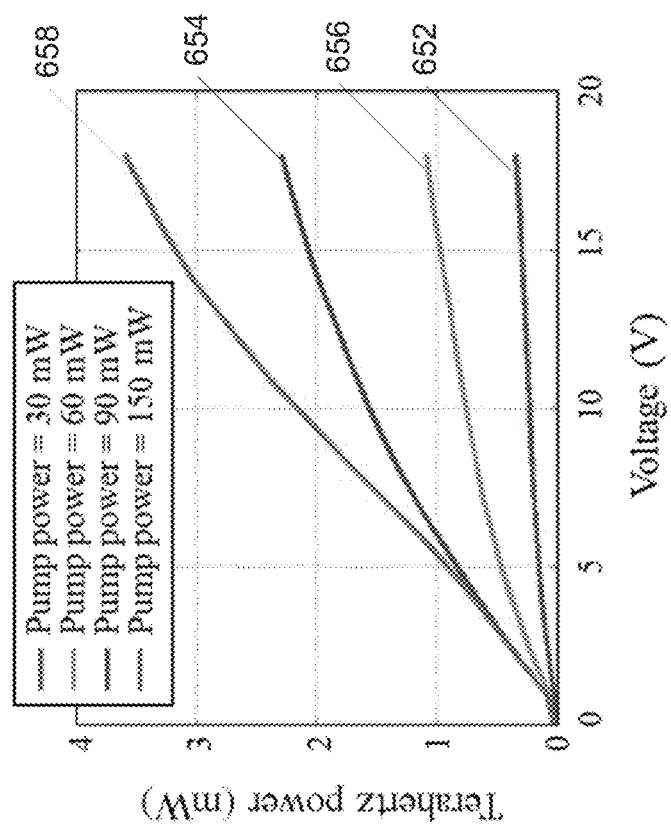
FIG. 6b is a graph illustrating radiated power from a plasmonic photoconductive source in accordance with an embodiment of the invention.

Scanning electron microscope (SEM) images of a fabricated large area plasmonic photoconductive source prototype in accordance with an embodiment of the invention is illustrated in FIG. 6a. The plasmonic photoconductive source prototype 600 can include a 5 µm plasmonic grating length 602 and the plasmonic contact electrode gratings incorporated inside the device active area. Terahertz radiation from the fabricated large area plasmonic photoconductive source can be characterized in response to an optical pump beam from a Ti:sapphire mode-locked laser at 800 nm wavelength, with a repetition rate of 76 MHz and a pulse width of 200 fs. Spot size of the optical pump beam can be adjusted to illuminate the entire device active area and polarization of the optical pump beam can be set to be normal to the plasmonic contact electrode gratings. A calibrated pyroelectric detector such as (but not limited to) a Spectrum Detector, Inc. SPI-A-65 THz can be used to measure radiated power as a function of the bias voltage and optical pump power. In many embodiments, a record-high terahertz radiation power of 3.6 mW can be detected at an optical pump power of 150 mW, exhibiting two orders of magnitude higher optical-to-terahertz conversion efficiencies compared to conventional large area photoconductive terahertz sources. A graph illustrating radiated power from a plasmonic photoconductive source in accordance with an embodiment of the invention is shown in FIG. 6b. The graph 650 illustrates the radiated terahertz power in mW as a function of voltage. The line 652 corresponds to a pump power of 30 mW, line 656 corresponds to a pump power of 60 mW, lines 654 corresponds to a pump power of 90 mW, and line 658 corresponds to a pump power of 150 mW.

Figure 7A:
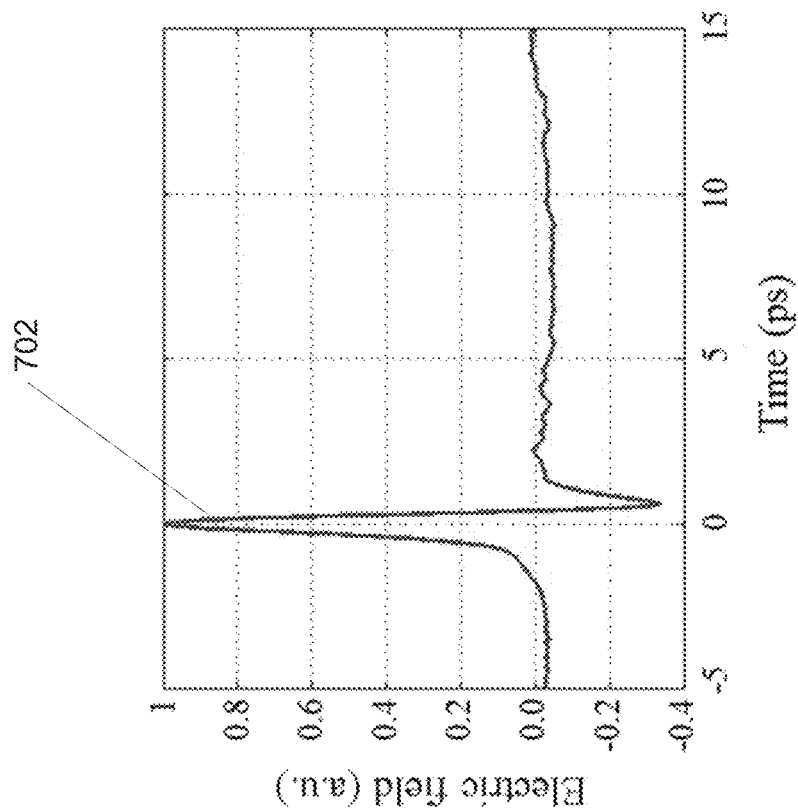
FIG. 7a is a graph illustrating a measured radiated field in the time domain in accordance with an embodiment of the invention.
Figure 7B:
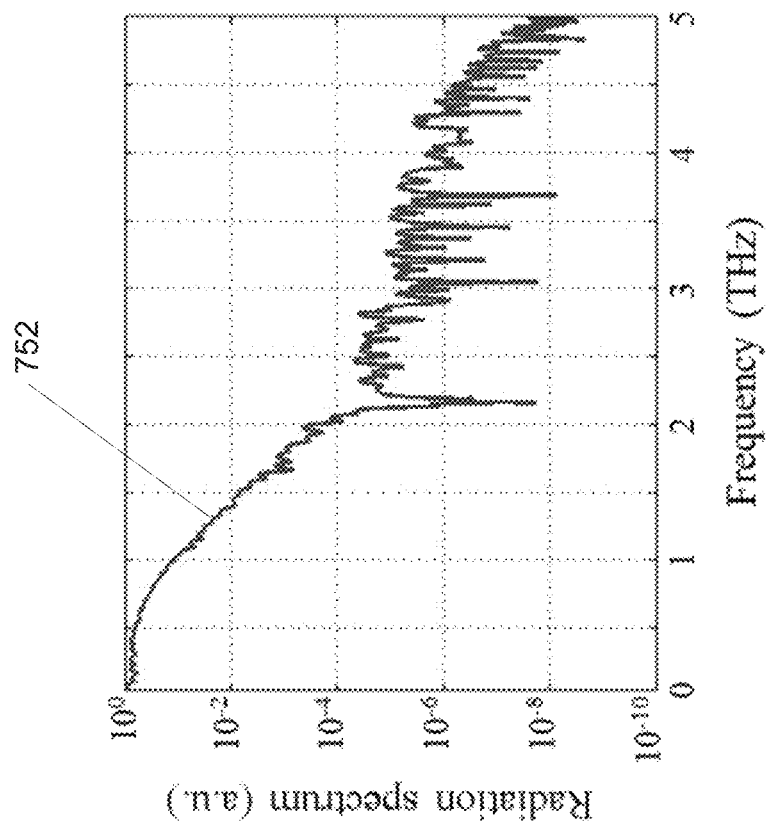
FIG. 7b is a graph illustrating a measured radiated field in the frequency domain in accordance with an embodiment of the invention.

The radiated electric field from the fabricated large area plasmonic photoconductive source can be characterized in a time-domain terahertz spectroscopy setup with electro-optic detection in a 1 mm thick ZnTe crystal. Measured time-domain radiated field and frequency-domain radiated power in accordance with an embodiment of the invention are shown in FIG. 7a and FIG. 7b, respectively. Graph 700 illustrates a time-domain radiated field of a large area plasmonic photoconductive source at 50 mW optical pump power. The radiated field 702 exhibits a terahertz radiation pulse width of 0.5 ps full width at half maximum (FWHM). Graph 750 illustrates a frequency-domain radiated power of a large area plasmonic photoconductive source at 50 mW optical pump power. The radiated power 752 shows a terahertz radiation spectrum in the 0.1-5 THz frequency range with more than 100 dB signal to noise ratio.

In several embodiments, the geometry of the large area plasmonic photoconductor for an array of terahertz sources and detectors fabricated on an ErAs:InGaAs substrate can be optimized with the highest terahertz radiation power and detection sensitivity, respectively, while maintaining a broad terahertz radiation/detection bandwidth. Use of ErAs:InGaAs substrates can allow operation at 1550 nm optical pump/probe wavelengths offered by the Advantest phase-modulated dual-femtosecond-laser system. Additionally, the short carrier lifetimes offered by the ErAs:InGaAs substrates can offer relatively lower noise floors for the large area plasmonic photoconductive terahertz sources and detectors, compared to other photo-absorbing substrates at 1550 nm wavelengths, by reducing the induced low frequency photocurrent.

In many embodiments, an array of 4×4 large area plasmonic photoconductive sources and an array of 3×3 large area plasmonic photoconductive detectors such that each terahertz detector is surrounded by four terahertz sources symmetrically can be utilized as illustrated in FIG. 3. Further, an area of 250×250 pmt can be selected for each source and detector. In various embodiments, the ErAs:InGaAs substrate can be mounted on a silicon lens with ~5 mm diameter, while centering the terahertz source/detector arrays in the center of the lens to have a radiation uniformity across the entire array. In addition, to align the fiber bundle relative to the terahertz source/detector array, the device can be mounted on a motorized XYZ translation stage and the optical alignment can be optimized iteratively using computer control and by maximizing the device photocurrent under an optical illumination. After reaching the optimum alignment, a UV-curable epoxy can be used to fix the position of the fiber bundle relative to the device.

Based on the above described configurations, the available optical pump/probe power from the Advantest phase-modulated dual-femtosecond-laser system and experimental results, signal-to-noise ratio of at least 80 dB for each large area plasmonic photoconductive detector in the 3×3 array should be achievable. Considering the terahertz absorption spectra of various biological tissue types, this can offer more than 3 mm detectable depth in biological tissue. It should be noted that the terahertz absorption and penetration depth varies for different types of biological tissue based on their structure and water content. Therefore, much deeper detectable depths are expected when using the proposed terahertz imaging system in the respiratory tract compared with gastrointestinal tract. Moreover, the expected radiation/detection bandwidth of the large area plasmonic photoconductive sources and detector is expected to accommodate resolving terahertz pulses with at least 0.5 ps pulse width, offering a depth resolution of less than ~30 um for the proposed terahertz imaging system. Additionally, a lateral resolution of ~0.5 mm can be expected for terahertz imaging systems in accordance with embodiments of the invention, which can be limited by the physical size of the large area plasmonic photoconductive detectors, numerical aperture of the silicon lens, and the diffraction limit. In many embodiments, design considerations can be estimated by assuming one axial scan for each pixel, which offers an image acquisition time of ~1 msec for the 3×3 pixels when using the Advantest phase-modulated dual-femtosecond-laser system. It should be noted that the signal-to-noise ratio of the terahertz imaging system can be improved by increasing the number of the axial scans and averaging the captured data. This offers an imaging system with higher signal-to-noise ratio levels and, thus, deeper penetration depths at the expense of reducing the image acquisition rate. Therefore, terahertz imaging systems in accordance with embodiments of the invention could have a transformative impact on the scope and potential use of terahertz imaging for a variety of tomography and hydration/inflammation measurements with potential application in the upper and lower gastrointestinal and respiratory tract.

In various embodiments, a deconvolution technique can be utilized to resolve the depth profile of each pixel from the temporal waveform of the reflected terahertz beam from each pixel. For this purpose, an array of terahertz sources as discussed above can be utilized to illuminate the surface of a flat gold mirror with terahertz pulses and record the reflected terahertz waveform at each pixel as a reference signal x(t). Assuming that the depth profile of each pixel is described by a temporal response h(t), the detected waveform at each pixel y(t) can be expressed as y(t)=h(t)*x(t). Therefore the depth profile of each pixel can be extracted from the temporal response of each pixel as:

$$h(t)=\Im^{-1}(y(\omega)/x(\omega))$$

Depending on the intensity of the reflected waveform, which might be very small at high frequency ranges of the terahertz spectrum, a window function (e.g. the Gaussian function) may be utilized to prevent error in the resolved image profile at the expense of losing high frequency data.

Since the overall size of the two dimensional array of plasmonic photoconductive sources and detectors can be limited by the endoscope tip's size constraints and due to the fact that there is typically not much benefit in reducing the dimension of each detector pixel beyond the diffraction limit in a noncontact imaging system, the total number of image pixels could be limited in many embodiments of the terahertz imaging system (i.e. 3×3). In developing further design considerations, systems with larger number of pixels can be explored and image processing techniques that would offer a larger field of view while using the 3×3 pixel array can also be considered. In various embodiments, in order to extend the overall field of view and resolve images with effectively larger number of pixels, image data from the terahertz imager can be processed with small number of pixels together with the higher resolution optical images captured by the optical camera (available at the tip of the endoscope) while moving the endoscope tip. In various embodiments, existing photography software packages can be used to overlap and stitch the captured optical and terahertz images and produce panoramic optical and terahertz images. Further, image cross registration algorithms can be utilized to map the high resolution optical images to the resolved terahertz images.

In many embodiments, terahertz imaging systems in accordance with embodiments of the invention can be tested on various low-loss multi-layered samples (e.g. stacks of paper, plastic, and paint) to characterize its signal-to-noise ratio and depth resolution. Such tests can assist in troubleshooting the developed image processing/reconstruction algorithms and procedures. In various embodiments, the terahertz imaging systems can be mounted on a flexible endoscope for imaging inside the respiratory and digestion tract of a carcass such as (but not limited to) that of a cow. It should be noted that phantoms specific to various biological tissues can be unavailable for the terahertz frequency range, and thus the most realistic samples to begin with could be organs from dead animals (e.g. cow lung and stomach). In this regard, the potential use of such high-performance terahertz imaging systems in accordance with embodiments of the invention can be explored on animal and human subjects. Some additional technical considerations and possible solutions are illustrated in Table I below.

TABLE I

| Considerations | Possible Solutions |
| --- | --- |
| Limitation of the lateral resolution of the image | Lateral image resolution can be improved by use of higher numerical aperture silicon lenses at the expense of increasing the device area at the endoscope tip. |
| Time-delay between adjacent fibers | Utilizing controllable phase modulators for each fiber channel and calibrating the phase modulators by use of a reference reflective surface. |
| Polarization sensitivity of plasmonic terahertz sources and detectors | Use of polarization maintaining fibers/splitters and preparing a fiber bundle to pump/probe the plasmonic terahertz sources and detectors at the optimum optical polarization. |
| Dispersion in the fiber bundle and splitters | Use of low-dispersion telecommunication fibers and minimizing the overall length of the fibers. |
| Low resistivity of ErAs:InGaAs substrate | Since low resistivity of the ErAs:InGaAs substrate can degrade the power of the terahertz source and increase the noise level of the terahertz detector, use of LT-GaAs and ErAs:GaAs can be explored, which have demonstrated promising performance at 1550 nm wavelengths for pulsed terahertz generation and detection. |

Although specific design considerations and data results are discussed above with respect to FIGS. 6a-7b and Table 1, any of a variety of designs and data results as appropriate to the requirements of a specific application can be utilized in accordance with embodiments of the invention. Terahertz sources and detectors for bronchoscopy in accordance with embodiments of the invention are discussed further below.

Terahertz Sources and Detectors For Bronchoscopy

Lung cancer is the deadliest cancer in North America and most of the developed world with an overall 5-year survival rate of less than 30% for different cancer stages. Terahertz bronchoscopy systems in accordance with embodiments of the invention can be utilized for early-stage lung cancer diagnosis and screening. Such systems can utilize plasmonic pulsed terahertz imaging techniques as described above and be compatible with minimally invasive, flexible bronchoscopy probes and advanced navigation modalities to offer real-time 3D tomographic images of airways, pulmonary nodules, and lung structure. In various embodiments, terahertz bronchoscopy systems can offer a depth resolution of ~50 um and a sub-millimeter lateral resolution revealing structural and shape information of much deeper peripheral nodules that cannot be detected by optical coherence tomography (OCT) and confocal microscopy (CFM). Further, terahertz bronchoscopy systems in accordance with embodiments of the invention could impact next generation pulmonary imaging toolset, enabling early-stage detection of lung cancer by providing more detailed information about the shape, size, physical and molecular structure of pulmonary nodules that cannot be scanned by OCT, CFM, and endobronchial ultrasound (EBUS), thus improving the likelihood ratio of targeting cancerous nodules in biopsy and surgery and improving therapy strategies.

As discussed above, terahertz waves do not pose an ionization hazard for human tissue due to their very low energy compared to shorter wavelength waves especially X-rays. Additionally, terahertz waves experience less scattering from biological tissue compared to optical waves due to their longer wavelengths, making it possible to see deeper into different biological tissue types. Moreover, several absorption lines of water and oxygen lie in the terahertz frequency spectrum, making terahertz waves very powerful means for distinguishing between tissues with different molecular/physical structure, hydration level, and hypoxia level, which are major sources of contrast between different tissue types (e.g. normal and malignant nodules). Another unique attribute of terahertz waves is their capability to identify molecules and biomarkers specific to special types of cancer, which can be an advantage in increasing the likelihood ratio of identifying cancerous nodules for improved therapy/biopsy/surgery strategies.

Figure 8:
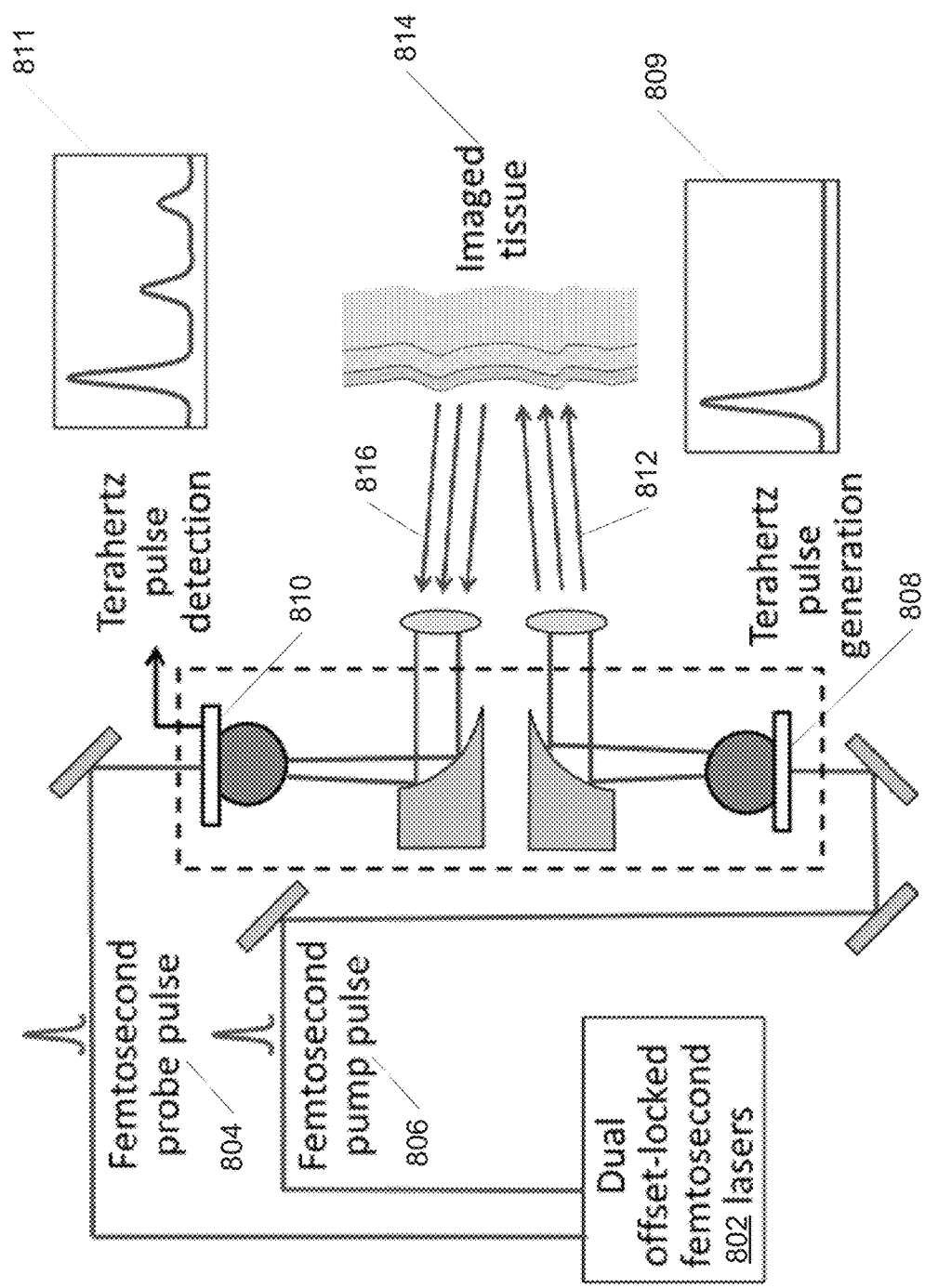
FIG. 8 is a schematic diagram of an asynchronous optical sampling (ASOPS) pulsed terahertz imaging system in accordance with an embodiment of the invention.

In bronchoscopy systems, pulsed terahertz imaging with asynchronous optical sampling (ASOPS) may be an appropriate scheme for resolving tissue images with high depth/thickness resolution and high image acquisition speeds. A schematic diagram of an ASOPS pulsed terahertz imaging system in reflection mode in accordance with an embodiment of the invention is shown in FIG. 8. The imaging system 800 includes two offset-locked femtosecond lasers 802 with different repetition rates 804 and 806 that pump/probe a photoconductive terahertz source 808 and/or detector 810 to generate 809 and/or detect 811 sub-picosecond terahertz pulses, respectively. The imaging process starts when the femtosecond optical pump pulse train from the pump mode-locked laser is incident on a photoconductive terahertz source 808 to generate a sub-picosecond terahertz pulse train, which is then focused 812 onto a specific spot on the imaged tissue 814. The reflected terahertz pulse 816 from the imaged tissue 814, which includes reflected echo pulses from different tissue layers, is then detected by use of a photoconductive terahertz detector 810 probed by the femtosecond optical probe pulse train from the probe mode-locked laser. The difference between the repetition rates of the optical pump and probe pulses allows adjusting the time-delay between the pump and probe optical beams and, thus, measuring the reflected signal from the imaged tissue in the time domain. Depth profile of the specific scanned spot on the imaged tissue is resolved by measuring the amplitude and timing of the reflected pulses. By scanning the position of the sub-picosecond terahertz pulse train across the tissue under test and resolving the depth profile of each scanned spot, a 3D image of the tissue is resolved. Although an ASOPS imaging modality combined with existing dual offset-locked femtosecond lasers allows resolving the depth profile of each image pixel in less than a 1 ms, the image acquisition time of existing terahertz imaging systems is still limited by the mechanical scanning process used in existing terahertz imaging systems. Additionally, the image depths offered by existing terahertz imaging systems are limited by low power levels and low sensitivity levels of available terahertz sources and detectors.

Although specific terahertz imaging techniques and devices for incorporation into bronchoscopy systems are discussed above with respect to FIG. 8, any of a variety of terahertz imaging systems as appropriate to the requirements of a specific application can be utilized in accordance with embodiments of the invention. Additional processes and devices for terahertz bronchoscopy systems in accordance with embodiments of the invention are discussed further below.

Terahertz Bronchoscopy Systems

A terahertz imaging modality based on plasmonic terahertz source/detector technology can be utilized to enhance the image depth and image acquisition time of existing terahertz imaging systems through a minimally-invasive, flexible bronchoscopy platform that can be used for but not limited to in vivo lung screening.

Figure 9A:
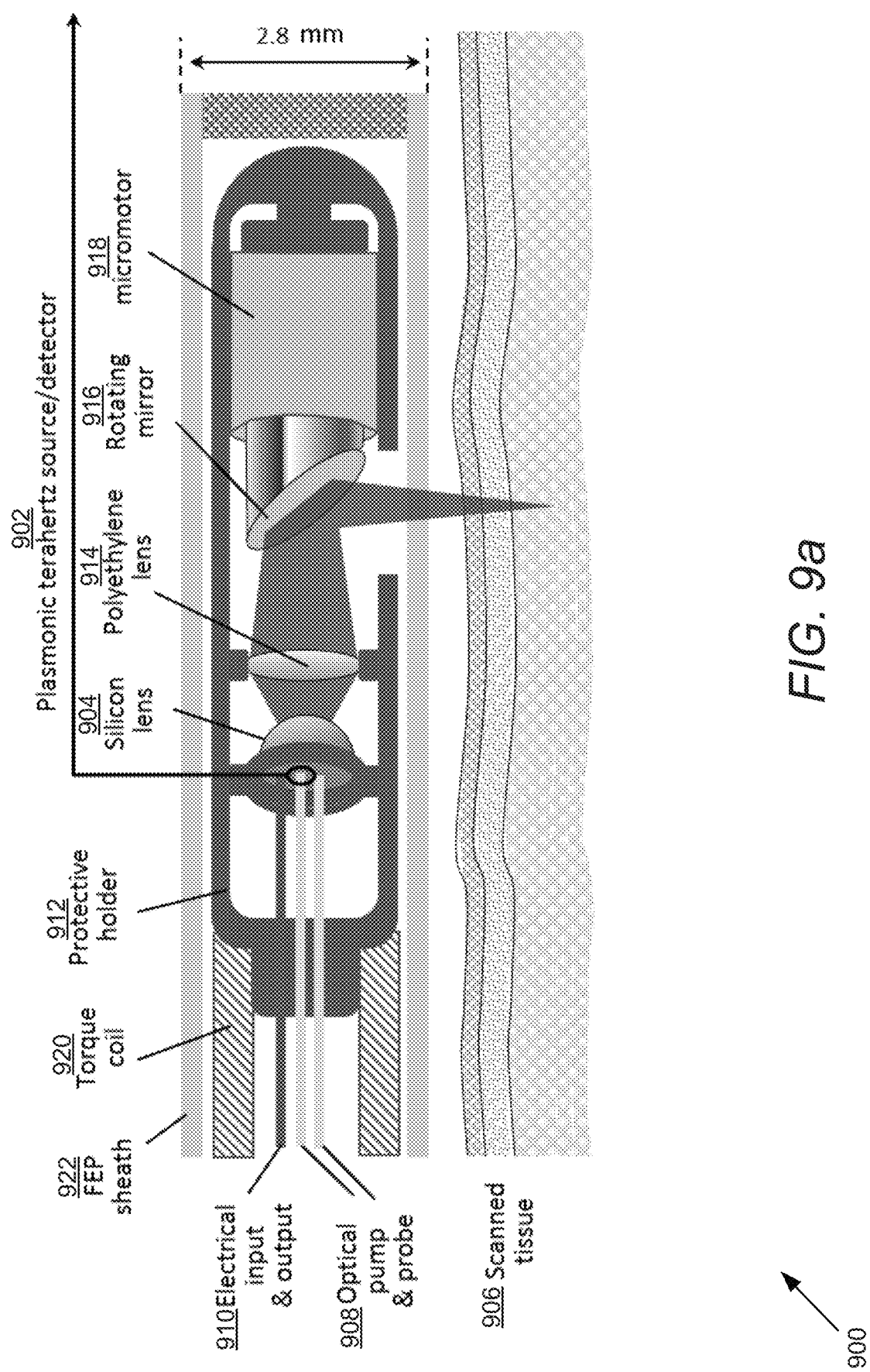
FIG. 9a illustrates a pulsed imaging system utilizing ASOPS in accordance with an embodiment of the invention.

A pulsed imaging system utilizing ASOPS in accordance with an embodiment of the invention is shown in FIG. 9a.

Figure 9B:
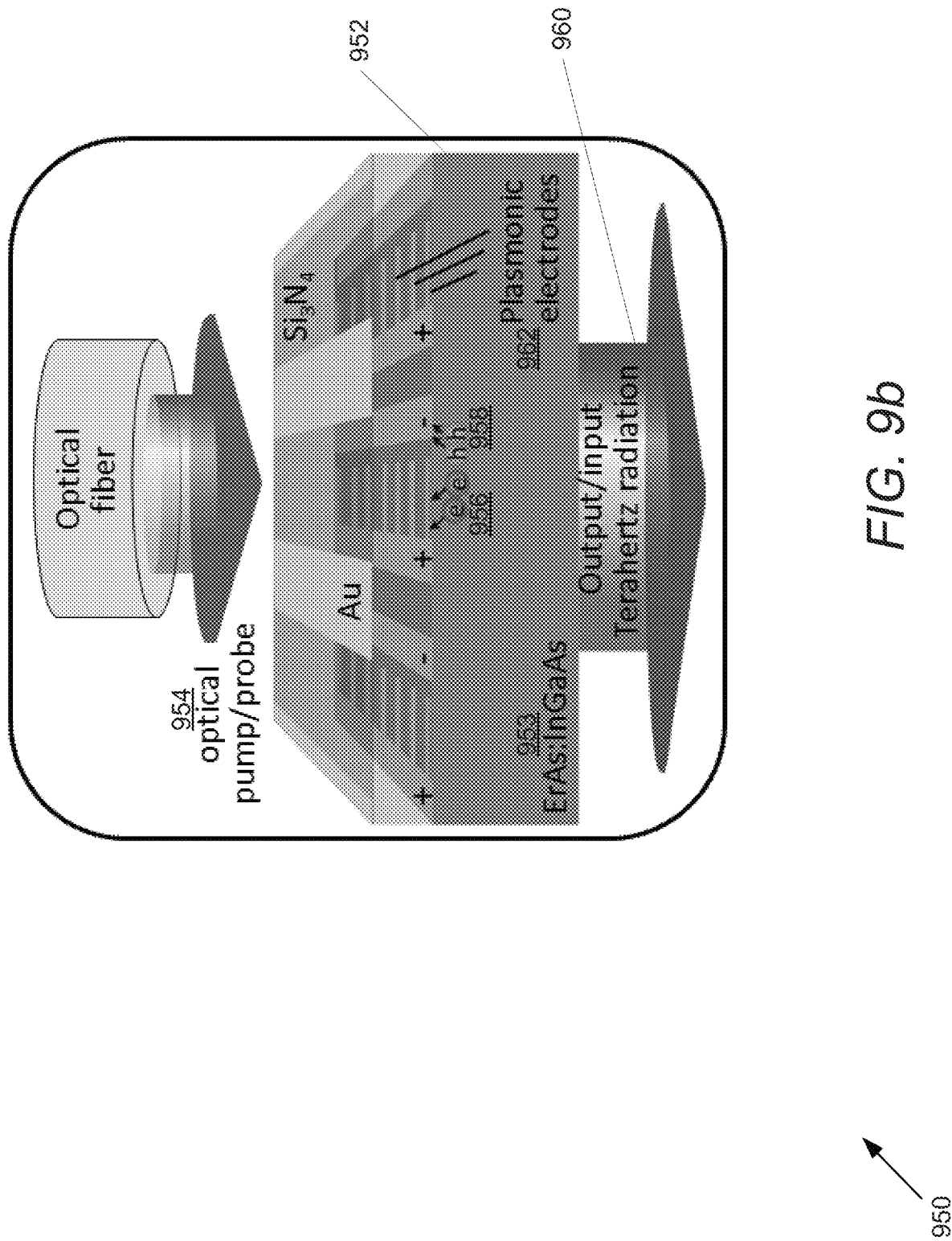
FIG. 9b is a schematic diagram and operation concept of a plasmonic terahertz source/detector in accordance with an embodiment of the invention.

In many embodiments, imaging system 900 can be utilized for resolving real-time, 3D images of lung tissue with more than 1 cm image depth, submillimeter lateral resolution and 50 um depth resolution. It is specifically designed to fit inside a narrow-diameter, flexible OCT-style catheter, compatible with the working channel of standard bronchoscopes for airway imaging. A key enabler of the imaging system can be a plasmonic terahertz source and detector 902 fabricated side by side on an ErAs:InGaAs substrate (as illustrated in FIG. 9b), mounted on a silicon lens 904. The plasmonic terahertz source and detector can be designed to operate at 1550 nm optical wavelengths to be compatible with low-dispersion fiber-coupled systems. In many embodiments, the plasmonic terahertz source and detector can be designed to produce 0.6 ps terahertz pulses with more than 3 mW power levels incident on the scanned tissue 906 and an overall signal-to-noise ratio of 100 dB for the detected pulses, which can offer more than 1 cm image depth and 50 um depth resolution. Two low-dispersion optical fibers connected to an external 1550 nm dual femtosecond laser system, carrying the pump and probe femtosecond pulses, can be packaged with the devices such that the pump and probe beams illuminate the active area of the plasmonic terahertz sources and detectors, respectively. The silicon lens 904, pump/probe fiber connectors 908 and the electrical input/output connectors 910 of the plasmonic sources and detectors can be mounted on a metallic protective holder 912 inside the catheter. In various embodiments, the radiated terahertz pulses can be focused onto the scanned tissue 906 through the silicon lens 904 and a polyethylene lens 914 mounted on the metallic protective holder. A rotating gold mirror 916 can be used to scan the normally-incident terahertz pulses on the lung tissue across the bronchial wall. For this purpose, the mirror can be mounted at a 45° angle on a micromotor 918, which can be mounted on the metallic protective holder inside the catheter. Typically, the reflected terahertz pulses from the tissue are reflected from the same gold mirror and focused onto the plasmonic terahertz detector 902 through the polyethylene 914 and silicon lenses 904. In several embodiments, the metallic protective holder can be used to fix the micromotor 918 to a torque coil 920. In addition, a FEP plastic sheath 922 can cover the metallic protective holder and micromotor 918. By pulling the metallic protective holder from the proximal end of the torque coil 920, a spiral scanning pattern could be achieved and a 3D image of the lung tissue along the bronchial tubes can be captured.

The terahertz imaging system can include plasmonic terahertz source and detector, which can be designed to have an active area of 0.5×0.5 mm². A schematic diagram and operation concept of a plasmonic terahertz source/detector in accordance with an embodiment of the invention is illustrated in FIG. 9b. The plasmonic terahertz source/detector 950 can include an active area 952 utilizing a ErAs:InGaAs substrate 953. When the active area of the plasmonic terahertz source is illuminated by an optical pump beam 954 photo-generated electrons 956 and holes 958 are accelerated in opposite directions by an external bias electric field. The acceleration and separation of the photocarriers induce a time-varying dipole moment within the device active area which generates terahertz radiation 960. Similarly, when the active area of the plasmonic detector is illuminated by an optical probe beam 954, photo-generated electrons 956 and holes 958 are accelerated in opposite directions by the received terahertz field 960 reflected from the imaged tissue. The acceleration and separation of the photocarriers induce a photocurrent within the device active area which is proportional to the received terahertz field.

Typically, the plasmonic terahertz source/detector design uses plasmonic contact electrodes 962 inside the device active area that concentrates the majority of the photocarriers in close proximity to the device contact electrodes to efficiently contribute to terahertz generation and detection. This can result in significantly higher terahertz radiation powers and detection sensitivities compared to conventional designs. In many embodiments, the such configurations have demonstrated more than two orders of magnitude terahertz power enhancement and more than one order of magnitude terahertz detection sensitivity enhancement by use of plasmonic contact electrodes.

In several embodiments, the design and geometry of the plasmonic device for a plasmonic terahertz source and detector fabricated on an ErAs:InGaAs substrate should be considered. Use of ErAs:InGaAs allows operation at 1550 nm optical pump/probe wavelengths at which low-dispersion fibers, fiber components, and fiber lasers are available. This allows maintaining short optical pump/probe widths and, therefore, short terahertz pulse widths in order to obtain 3D terahertz images with a high depth resolution. Additionally, short carrier lifetime of ErAs:InGaAs offers relatively lower noise floors for the plasmonic terahertz sources and detectors, compared to other photo-absorbing substrates at 1550 nm wavelengths, by reducing the induced low frequency photocurrent.

In various embodiments, the performance of a variety of plasmonic terahertz source/detector geometries and architectures to study the tradeoffs between terahertz radiation power and detection sensitivity relative to the terahertz radiation/detection bandwidth for each design can be investigated to determine designs with highest terahertz radiation power levels, detection sensitivity levels, and terahertz generation/detection bandwidths to maximize the imaging depth, image contrast (signal-to-noise ratio), and image resolution. In various embodiments, image contrast and image depth may degrade with polarization variability of the optical pump/probe pulses due to fiber bending/stretching effects. Further, since plasmonic contact electrodes utilized in the plasmonic terahertz sources and detectors can polarization sensitive, variations in optical pump/probe polarization can degrade terahertz radiation power and detection sensitivity levels. Thus, the use of new types of plasmonic contact electrode structures with symmetric geometries (e.g. periodic nanoscale cross-shapes and ring-shape structures rather than nanoscale gratings), which would exhibit polarization-independent optical absorption/enhancement should be considered.

Although specific terahertz bronchoscopy systems are discussed above with respect to FIGS. 9a-b, any of a variety of terahertz bronchoscopy systems utilizing plasmonic terahertz sources and detectors as appropriate to the requirements of a specific application can be utilized in accordance with embodiments of the invention. Terahertz bronchoscopy design considerations and performance in accordance with embodiments of the invention are discussed further below.

Terahertz Bronchoscopy Performance and Design Considerations

In many embodiments, 0.6 ps terahertz pulses with 50 MHz repetition rate and more than 3 mW power levels with 100 dB signal-to-noise ratio levels can be achieved by use of the proposed plasmonic terahertz sources/detectors pumped/probed by the dual femtosecond laser system. Based on these specifications and measured characteristics of human lung tissue, predictions for the performance of the proposed terahertz bronchoscopy system can be made. As discussed above, the depth resolution of the resolved image can be determined by the pulse width of the incident terahertz pulses inside the imaged tissue, which is estimated as ~c. $\Delta t/(2n)$, where c is the speed of light, $\Delta t$ is the pulse-width of the incident terahertz pulse on the tissue ($\Delta t$~0.6 ps), and n is the effective refractive index of the tissue (2.2–1.8 in the 0.1-2 THz frequency range). Therefore, a depth resolution of ~50 um can be expected in several embodiments of the pulsed imaging system, which is much better than the depth resolution offered by CT. In addition, the image depth can be estimated as ~1.16 log(SNR)/$\alpha$, where SNR is the signal-to-noise ratio of the imaging system, a is the linear absorption coefficient of the tissue (0.5-12 $cm^{-1}$ in the 0.1-2 THz frequency range). Thus, an image depth of ~1 cm can be predicted for the terahertz bronchoscopy system, which is ~3 times larger than the image depth offered by OCT.

In various embodiments, the absorption spectra of different types of lung tissue samples over a broader terahertz frequency range can be measured and the results used for making more accurate predictions for the image depth of the system. In some embodiments, the lateral resolution of the resolved image can be limited by diffraction and, thus, determined by the effective wavelength of the incident terahertz beam inside the imaged tissue and numerical aperture and aberration of the utilized lenses. Therefore, a sub-millimeter lateral image resolution can be estimated when imaging lung tissues, which is comparable with the lateral resolution of CT and EBUS images. Additionally, axial scanning speeds as fast as 1 msec/scan can be offered by commercially available dual femtosecond laser that can be utilized in various embodiments. Considering availability of micromotors with 1200-7200 rpm speeds, much higher imaging frame rates can be offered by the proposed terahertz imaging system compared to conventional systems that use mechanical raster scanning. It should be noted that multiple scans can be used for capturing the depth profile of each specific spot of the tissue with higher signal-to-noise ratios, resulting in a tradeoff between image quality and acquisition time.

In addition, plasmonic terahertz sources and detectors can be fabricated on ErAs:InGaAs substrates because of their high optical absorption at 1550 nm optical wavelength and their short carrier lifetime levels required for generation/detection of very short terahertz pulses while suppressing background low-frequency photocurrent of the device for maintaining a low noise operation. Typically, the fabrication process begins with patterning the plasmonic contact electrodes using electron-beam lithography, followed by metal deposition and liftoff. An optical lithography step can be used to pattern the bias lines, which is followed by metal deposition and liftoff. In many embodiments, a $Si_3N_4$ anti-reflection coating can be deposited using plasma-enhanced chemical vapor deposition. A shadow metal layer can be patterned next through optical lithography, followed by metal deposition and liftoff. Contact vias can be patterned using optical lithography and opened by etching the $Si_3N_4$ layer using reactive ion etching. In various embodiments, the devices can be then mounted on a silicon lens and input/output electrical wires bonded to the contact vias. The silicon lens can be temporarily mounted on a rotation mount to connect the optical pump/probe fibers to the plasmonic terahertz source/detector. For this purpose, each fiber is typically placed inside a fiber holder on a XYZ translation stage and optical alignment is optimized iteratively for each fiber using computer control and by maximizing the device photocurrent under an optical illumination. After reaching the optimum alignment, a UV-curable epoxy can be used to fix the position of each fiber relative to the device.

In several embodiments, the terahertz power, terahertz pulse width, and signal-to-noise ratio of the imaging systems should be characterized before integrating the device with a suitable catheter. The radiated power can be measured by a calibrated pyroelectric detector. In order to measure terahertz pulse width and signal-to-noise ratio, the silicon lens can be placed in front of a flat gold mirror to have the generated terahertz pulses normally incident on the mirror. The reflected terahertz beam can then be measured in the time domain and terahertz pulse width and signal-to-noise ratio of the imaging system is calculated accordingly. The optimum location of the polyethylene lens can be determined in this process by maximizing the signal-to-noise ratio of the imaging system. In many embodiments, the process is repeated when adding the rotating mirror at 45 degrees angle changing the terahertz beam path by 90 degrees, compatible with the proposed system shown in FIG. 9a. The size and geometry of the lenses can be chosen such that the whole silicon lens/polyethylene lens/rotting mirror system fits in a 2-3 mm diameter catheter with a 1 cm length, while providing a sub-millimeter terahertz beam size within a 2 cm distance from the edge of the rotating mirror. Further, terahertz beam size at different distances can be measured by knife-edge technique. In various embodiments, the performance of the imaging system can be characterized for resolving the depth profile of fresh human lung tissue samples. For this purpose, the temporal waveform of the reflected terahertz beam from each scanned spot can be captured through a lock-in amplifier in form of a digital data and continuously stored by use of a 64-bit computer with 32 GB memory, while scanning different spots on the tissue samples.

As discussed above, signal processing can be performed using a deconvolution technique to resolve the depth profile of each imaged spot from the temporal waveform of the reflected terahertz beam from that spot. One challenge in resolving the depth profile can be various reflections in the imaging system, which might be falsely interpreted as reflections from tissue layers. To address this challenge, signal processing techniques can be optimized before integrating the terahertz imaging system with the catheter and by use of a linear scan. In various embodiments, the terahertz imaging system can be used to illuminate the surface of a flat gold mirror and record the reflected terahertz waveform as a reference signal x(t). Assuming that the depth profile is described by a temporal response h(t), the detected waveform can be expressed as y(t)=h(t)*x(t). Therefore, the depth profile of the scanned tissue spot can be extracted from the temporal response as h(t)=$\mathfrak{S}^{-1}$(y($\omega$)/x($\omega$)), where t and $\omega$ represent time and angular frequency, respectively. Depending on the intensity of the reflected waveform, which might be very small at high frequency ranges of the terahertz spectrum, a window function (e.g. the Gaussian function) may be used to prevent error in the resolved image profile at the expense of losing high frequency data. By a linear scanning along the lung tissue sample, a cross-sectional image profile of the lung tissue sample can be resolved and compared with tissue histology to assess the image depth, depth resolution, and contrast of the developed imaging system.

In several embodiments, the imaging system can be integrated with a catheter. Packaging the proposed terahertz imaging system within a 2-3 mm diameter, 1 cm long catheter can be a challenging task. Since the size and distance of the components are comparable with terahertz wavelengths, the performance of the proposed imaging system will be affected by spatial misalignments between components. To address this challenge, the diameters of the silicon lens, polyethylene lens, rotating mirror, and micromotor can be set to match the diameter of a series of threads perforated inside a metallic protective holder at the optimum distanced determined in previous terahertz imaging characterization steps. The protective holder can be built from two complementary half tubes. Thus, the whole system can be put together by placing the silicon lens, polyethylene lens, rotating mirror, micromotor, and torque coil inside the first protective half-tube at the designated locations specified by the threads followed by the second protective half-tube covering the rest of the package. The gaps between the two metallic half tubes are filled with a UV-curable epoxy and the whole package is placed inside a FEP sheath. Terahertz bronchoscopy design implementation and considerations in accordance with embodiments of the invention are discussed further below.

System Characterization

Figure 10:
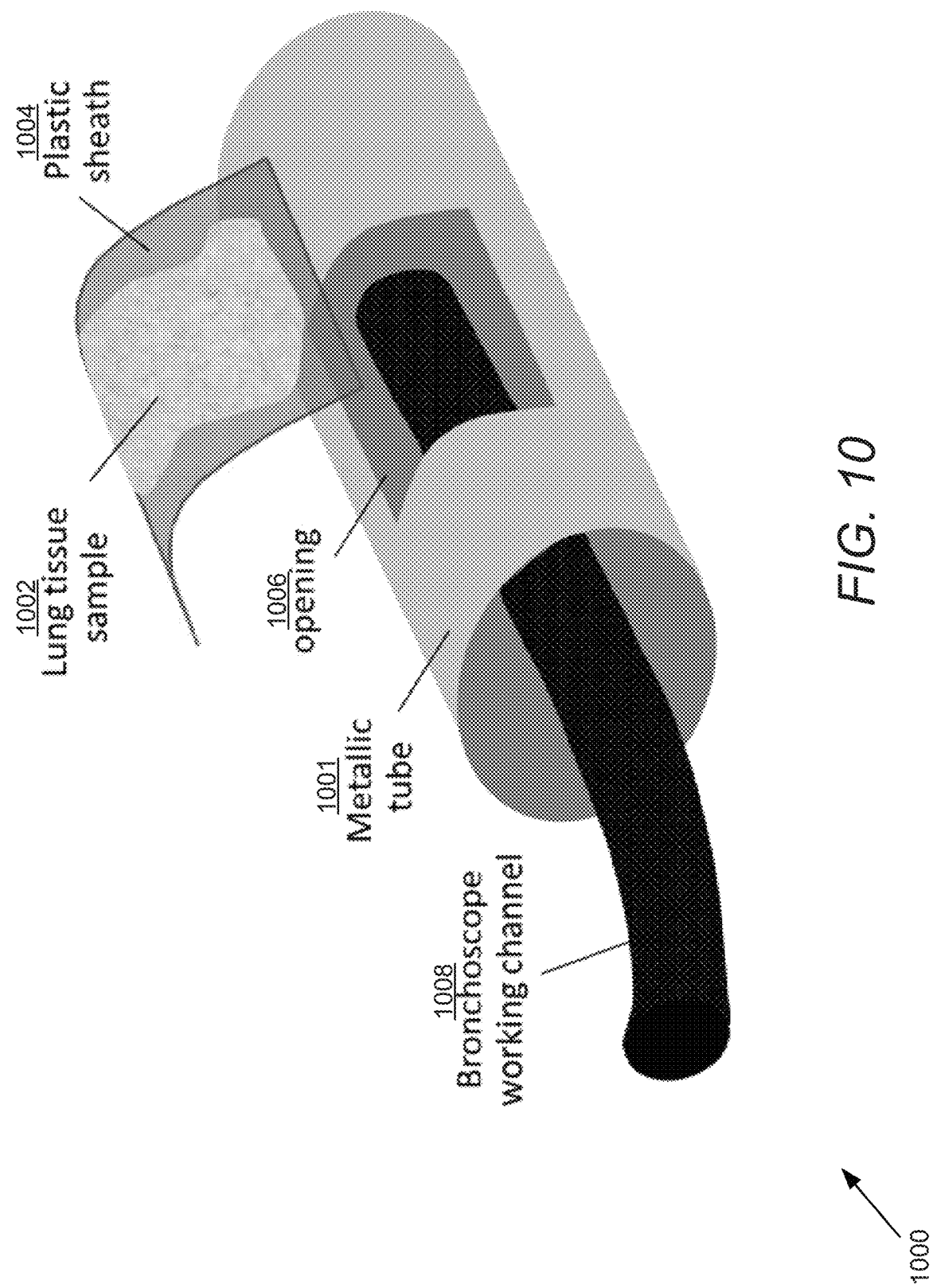
FIG. 10 illustrates a testing apparatus comprising a metallic tube with a cut-through opening in accordance with an embodiment of the invention.

In many embodiments, terahertz imaging system for bronchoscopy can be employed utilizing a flexible bronchoscope with a 2.8 mm diameter working channel. A testing apparatus comprising a metallic tube with a cut-through opening can be used to represent a bronchial channel as illustrated in FIG. 10. The apparatus 1000 can include a metallic tube 1001. In various embodiments, human lung tissue samples 1002 can be placed on a plastic sheath 1004 that can be configured to cover an opening 1006. The bronchoscope carrying the terahertz scanner can be inserted into the metallic tube 1001 to capture a 3D image of the lung tissue sample 1002 within the opening area 1006. The diameter of the catheter covering the terahertz imaging system can be set to be less than 2.8 mm to fit into the working channel of the bronchoscope 1008. The diameter of the metallic tube 1001 can be set to be slightly larger than the bronchoscope diameter.

In various embodiments, tissue samples can be extracted in surgery, which contain various types of malignant and non-malignant nodules. Since the imaging modality is in reflection mode, there is no specific requirement for the thickness of the tissue samples. This allows a fast sample preparation process and maintaining most of the tissue water content to achieve realistic terahertz images. The resolved terahertz images can be compared with tissue histology to evaluate contrast ratios of normal tissue and malignant/non-malignant nodules as well as the image depth and lateral/depth resolution.

A consideration in resolving 3D terahertz images can be etalon effects due to multiple reflections between the FEP sheath interfaces and the surface of the scanned tissue. The negative impact of these effects can be eliminated through the calibration process described in the signal processing section above. However, the calibration process can be sensitive to the spacing between the tissue and FEP sheath, which can be hard to maintain in realistic settings. To address this challenge, the calibration process performed using a reflective gold mirror can be conducted for all possible distances between the FEP sheath and tissue surface (0.1-4 mm range) with a distance step size less than 50 um and the measured calibration data is recorded. When processing the image data from human lung tissue samples, the distance between the sheath and tissue surface can be estimated by measuring the time delay of the first echo pulse reflected from the surface of the tissue and the calibration data corresponding the measured distance is used for resolving terahertz images.

Another consideration in the process of lung tissue characterization is maintaining tissue freshness, since the tissue water content would be a crucial factor in determining the terahertz signal penetration depth in the tissue and the image depth accordingly. Thus, various tissue taping/sealing techniques to maintain tissue freshness over longer times should be considered, while planning a carefully organized coordination between various tissue transfer and measurement steps. In the meantime, the significant impact of sample freshness should not be ignored when assessing the performance of the developed terahertz bronchoscopy system for in vivo lung screening. Additionally, other factors that will not be accounted for in an evaluation platform using replica models of a bronchial channel can include the motion artifacts secondary to cardiac pulsations and respiratory movements. Thus terahertz bronchoscopy systems in accordance with embodiments of the invention should be evaluated for in vivo lung screening using animal/human subjects through various collaborative clinical/translational research projects.

Although specific employment and testing apparatus for terahertz bronchoscopes are discussed above with respect to FIG. 10, any of a variety of terahertz bronchoscopes and testing apparatus as appropriate to the requirements of the a specific application can be utilized in accordance with embodiments of the invention. While the above description contains many specific embodiments of the invention, these should not be construed as limitations on the scope of the invention, but rather as an example of one embodiment thereof. It is therefore to be understood that the present invention may be practiced otherwise than specifically described, without departing from the scope and spirit of the present invention. Thus, embodiments of the present invention should be considered in all respects as illustrative and not restrictive.

What is claimed is:

1. A terahertz imaging system for endoscopy, comprising:
a terahertz imager configured to receive terahertz image data comprising:
a fiber bundle;
at least one terahertz source configured to generate terahertz radiation, wherein each of the at least one terahertz source has an active area having at least one plasmonic contact electrode that can be illuminated by optical pump beams to generate the terahertz radiation; and
at least one terahertz detector configured to receive terahertz field data, wherein each of the at least one terahertz detector has an active area having at least one plasmonic contact electrode that can be illuminated by optical pump beams to induce an output proportional to the received terahertz field; and
wherein the at least one terahertz source and detector are arranged in a two dimensional array such that each terahertz detector is surrounded by a plurality of terahertz sources symmetrically; and
wherein the fiber bundle couples optical pump beams to the active area of the at least one terahertz source and optical probe beams to the active area of the at least one terahertz detector.

2. The terahertz imaging system of claim 1, further comprising an optical light source configured to illuminate at least one target.

3. The terahertz imaging system of claim 2, further comprising an optical camera configured to receive optical image data related to the illuminated target.

4. The terahertz imaging system of claim 1, further comprising a laser source configured to pump the at least one terahertz source and to probe the at least one terahertz detector using femtosecond optical beams.

5. The terahertz imaging system of claim 4, wherein the laser source is a phase-modulated dual-laser-synchronized control femtosecond laser.

6. The terahertz imaging system of claim 1, wherein the at least one terahertz source and detector are fabricated on an InGaAs substrate.

7. The terahertz imaging system of claim 1, wherein the at least one terahertz source and detector are fabricated on a GaAs substrate.

8. The terahertz imaging system of claim 1, further comprising an electrical input to the at least one terahertz source to generate a bias voltage.

9. The terahertz imaging system of claim 1, further comprising an electrical output from the at least one terahertz detector configured to collect the output from the at least one terahertz detector.

10. The terahertz imaging system of claim 1, wherein the at least one terahertz source and detector are mounted on a silicon lens.

11. The terahertz imaging system of claim 1, wherein the at least one terahertz source and detector are arranged in an array such that each terahertz detector is surrounded by four terahertz sources symmetrically.

12. The terahertz imaging system of claim 3, wherein image data is collected simultaneously from the optical camera and the terahertz imager.

13. The terahertz imaging system of claim 12, wherein at least one panoramic image is generated from the optical image data and terahertz image data using cross registration algorithms to map the optical image data to the terahertz image data.

14. The terahertz imaging system of claim 13, wherein the at least one terahertz source and detector are compatible with 1550 nanometer optical wavelengths.

15. The terahertz imaging system of claim 13, wherein the at least one terahertz source and detector are compatible with at least one of: 800 nanometer optical wavelengths and 1000 nanometer optical wavelengths.

16. The terahertz imaging system of claim 1, further comprising at least one optical lens.

17. A terahertz imaging system for endoscopy, comprising:
    a terahertz imager configured to receive terahertz image data comprising:
        a fiber bundle;
        at least one terahertz source configured to generate terahertz radiation, wherein each of the at least one terahertz source has an active area that can be illuminated by optical pump beams to generate the terahertz radiation; and
        at least one rotating element configured to reflect the generated terahertz radiation across scanned material;
        at least one terahertz detector configured to receive terahertz radiation reflected by the at least one rotating element, wherein each of the at least one terahertz detector has an active area that can be illuminated by optical probe beams to induce an output proportional to the received terahertz field;
    wherein the at least one terahertz source and detector are arranged in a two-dimensional array such that each terahertz detector is surrounded by a plurality of terahertz sources symmetrically;
    wherein the fiber bundle couples optical pump beams to the active area of the at least one terahertz source and optical probe beams to the active area of the at least one terahertz detector; and
    wherein the at least one terahertz source, at least one rotating element, and at least one terahertz detector are arranged in a catheter.

18. The terahertz imaging system of claim 17, wherein the at least one rotating element is a mirror mounted at a particular angle on a micromotor within the catheter.

19. The terahertz imaging system of claim 18, wherein the micromotor can rotate the at least one rotating element during reflection of the generated terahertz radiation across the scanned material.

20. The terahertz imaging system of claim 17, wherein:
    the at least one terahertz source has at least one plasmonic contact electrode; and
    the at least one terahertz detector has at least one plasmonic contact electrode.

* * * * *